US012790559B2

(12) United States Patent
Kato et al.

(10) Patent No.: US 12,790,559 B2
(45) Date of Patent: *Nov. 10, 2026

(54) FLUORINE-CONTAINING ETHER COMPOUND, LUBRICANT FOR MAGNETIC RECORDING MEDIUM, AND MAGNETIC RECORDING MEDIUM

(71) Applicant: SHOWA DENKO K.K., Tokyo (JP)

(72) Inventors: Tsuyoshi Kato, Ichihara (JP); Ayano Asano, Ichihara (JP); Natsumi Shibata, Ichihara (JP); Daisuke Yagyu, Ichihara (JP); Takuma Kuroda, Ichihara (JP); Naoya Fukumoto, Ichihara (JP)

(73) Assignee: Resonac Corporation, Tokyo (JP)

( * ) Notice: Subject to any disclaimer, the term of this patent is extended or adjusted under 35 U.S.C. 154(b) by 206 days.

This patent is subject to a terminal disclaimer.

(21) Appl. No.: 18/009,371

(22) PCT Filed: Jun. 7, 2021

(86) PCT No.: PCT/JP2021/021500
§ 371 (c)(1),
(2) Date: Dec. 9, 2022

(87) PCT Pub. No.: WO2021/251318
PCT Pub. Date: Dec. 16, 2021

(65) Prior Publication Data

US 2024/0002743 A1 Jan. 4, 2024

(30) Foreign Application Priority Data

Jun. 11, 2020 (JP) ................................ 2020-101575

(51) Int. Cl.
*C10M 131/10* (2006.01)
*C07C 43/12* (2006.01)
(Continued)

(52) U.S. Cl.
CPC ......... *C10M 131/10* (2013.01); *C07C 43/126* (2013.01); *G11B 5/7257* (2020.08); *C10M 2211/0425* (2013.01); *C10N 2040/18* (2013.01)

(58) Field of Classification Search
CPC .............. C10M 105/54; C10M 131/10; C10M 2213/00; C10M 2213/04; C10M 2213/043;
(Continued)

(56) References Cited

U.S. PATENT DOCUMENTS 4,526,833 A 7/1985 Burguette et al.
11,261,394 B2 * 3/2022 Kato ................... C10M 107/38
(Continued)

FOREIGN PATENT DOCUMENTS

JP 11-60720 A 3/1999
JP 2009-266360 A 11/2009
(Continued)

OTHER PUBLICATIONS

Derwent Abstract of WO 2019054148.*
(Continued)

*Primary Examiner* — Holly Rickman
*Assistant Examiner* — Lisa Chau
(74) *Attorney, Agent, or Firm* — Sughrue Mion, PLLC

(57) ABSTRACT

A fluorine-containing ether compound represented by the following formula. $R^1—R^2—O—$ $CH_2—R^3—CH_2—O—R^4—R^5$ ($R^3$ is a perfluoropolyether chain; $R^2$ is represented by Formula (2), $R^4$ is represented by Formula (3), $R^1$ and $R^5$ are hydrogen atoms or Formula (4); a and b in Formula (2) are an integer of 0 to 2, c in Formula (2) is an integer of 2 to 5, d and e in Formula (3) are an integer of 0 to 2, f in Formula
(Continued)

(3) is an integer of 2 to 5; at least one of b in Formula (2) and e in Formula (3) is 1 or more; and k in Formula (4) is an integer of 3 to 6.)

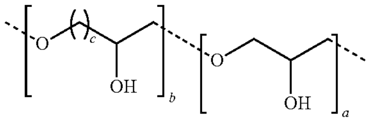

(2)

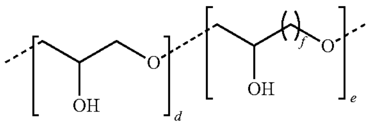

(3)

$HO—(CH_2)_k—$ (4)

5 Claims, 1 Drawing Sheet

(51) Int. Cl.
*G11B 5/725* (2006.01)
*C10N 40/18* (2006.01)

(58) Field of Classification Search
CPC ...... C10M 2213/06; C10M 2213/0606; C10N 2040/18; G11B 5/725–7257
See application file for complete search history.

(56) References Cited

U.S. PATENT DOCUMENTS

2010/0233513 A1 9/2010 Imai et al.
2010/0261039 A1 10/2010 Itoh et al.
2012/0225217 A1 9/2012 Itoh et al.
2013/0209837 A1 8/2013 Sagata et al.
2017/0260472 A1 9/2017 Sagata et al.
2021/0062102 A1* 3/2021 Kato .................. G11B 5/73911

FOREIGN PATENT DOCUMENTS

JP 2010-143855 A 7/2010
JP 4632144 B2 2/2011
JP 2012-9090 A 1/2012
JP 2013-163667 A 8/2013
JP 5465454 B2 4/2014
JP 5786047 B2 9/2015
JP 5909837 B2 4/2016
JP 2018-24614 A 2/2018
WO 2009/035075 A1 3/2009
WO 2016/084781 A1 6/2016
WO 2017/145995 A1 8/2017
WO 2019/049585 A1 3/2019
WO 2019/054148 A1 3/2019

OTHER PUBLICATIONS

International Search Report for PCT/JP2021/021500 dated, Aug. 17, 2021 (PCT/ISA/210).
International Search Report for PCT/JP2018/031161 dated, Nov. 27, 2018 (PCT/ISA/210).
Non-Final Office Action dated Jul. 23, 2021, issued in U.S. Appl. No. 16/644,586.
Notice of Allowance dated Nov. 9, 2021, issued in U.S. Appl. No. 16/644,586.
Supplemental Notice of Allowance dated Dec. 2, 2021, issued in U.S. Appl. No. 16/644,586.

* cited by examiner

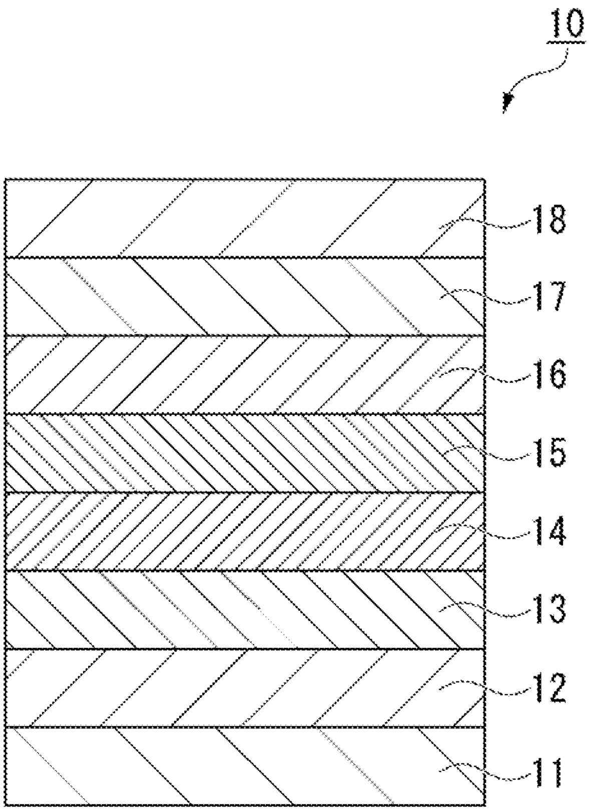
10
18
17
16
15
14
13
12
11

FLUORINE-CONTAINING ETHER COMPOUND, LUBRICANT FOR MAGNETIC RECORDING MEDIUM, AND MAGNETIC RECORDING MEDIUM

CROSS REFERENCE TO RELATED APPLICATIONS

This application is a National Stage of International Application No. PCT/JP2021/021500 filed Jun. 7, 2021, claiming priority based on Japanese Patent Application No. 2020-101575 filed Jun. 11, 2020.

TECHNICAL FIELD

The present invention relates to a fluorine-containing ether compound, a lubricant for a magnetic recording medium, and a magnetic recording medium.

Priority is claimed on Japanese Patent Application No. 2020-101575, filed Jun. 11, 2020, the content of which is incorporated herein by reference.

BACKGROUND ART

Development of magnetic recording media suitable for high recording densities is underway to improve the recording densities of magnetic recording/reproducing devices.

As a conventional magnetic recording medium, there is a magnetic recording medium in which a recording layer is formed on a substrate and a protective layer made of carbon or the like is formed on the recording layer. The protective layer protects information recorded in the recording layer and enhances the slidability of a magnetic head. In addition, the protective layer covers the recording layer to prevent metal contained in the recording layer from being corroded by environmental substances.

However, sufficient durability of the magnetic recording medium cannot be obtained by simply providing the protective layer on the recording layer. Therefore, a lubricant is applied to the surface of the protective layer to form a lubricating layer with a thickness of about 0.5 to 3 nm. The lubricating layer improves the durability and protective power of the protective layer and prevents contamination substances from intruding into the magnetic recording medium.

After forming the lubricating layer on the surface of the protective layer, a burnishing step may be performed to remove projections and particles present on the surface of the magnetic recording medium and improve the smoothness of the surface.

As a lubricant that is used at the time of forming a lubricating layer in a magnetic recording medium, there is, for example, a lubricant containing a fluorine-based polymer having a repeating structure containing $—CF_2—$ and having a polar group such as a hydroxyl group at a terminal.

For example, Patent Documents 1 to 4 disclose a magnetic recording medium containing a lubricating layer containing a perfluoropolyether having hydroxyl groups at terminals.

CITATION LIST

Patent Document

Patent Document 1: Japanese Patent No. 5786047

Patent Document 2: Japanese Patent No. 4632144

Patent Document 3: PCT International Publication No. WO2019/054148

Patent Document 4: PCT International Publication No. WO2019/049585

SUMMARY OF INVENTION

Technical Problem

There is a demand for a further decrease in the flying height of a magnetic head in magnetic recording/reproducing devices. This requires a further decrease in the thickness of protective layers and lubricating layers in magnetic recording media.

However, if the thickness of protective layers and/or lubricating layers is reduced, the corrosion resistance of magnetic recording media may become insufficient. In particular, in a case where tape burnishing is performed on the surface of a magnetic recording medium after forming a lubricating layer, the corrosion resistance of the magnetic recording medium is likely to be insufficient. For this reason, there is a demand for a lubricating layer which is highly effective in suppressing corrosion of magnetic recording media.

The present invention has been made in consideration of the above circumstances, and an object of the invention is to provide a fluorine-containing ether compound that can be used as a material for a lubricant for a magnetic recording medium with which a lubricating layer highly effective in suppressing corrosion of a magnetic recording medium can be obtained.

In addition, another object of the present invention is to provide a lubricant for a magnetic recording medium containing the fluorine-containing ether compound of the present invention.

In addition, still another object of the present invention is to provide a magnetic recording medium which has a lubricating layer containing the fluorine-containing ether compound of the present invention and has excellent corrosion resistance.

Solution to Problem

The present inventors have conducted extensive studies in order to solve the above-described problem.

As a result, they have found that a fluorine-containing ether compound may suffice in which a linking group with a specific structure, in which an ether bond (—O—), two or more linearly bound methylene groups ($—(CH_2)_q—$ (q in the formula is an integer of 2 to 5)), a methylene group in which one hydrogen atom is substituted with a hydroxyl group (—CH(OH)—), and a methylene group ($—CH_2—$) are combined, is placed between a terminal hydroxyl group (—OH) and one or both end portions of a perfluoropolyether chain, thus leading to realization of the present invention.

That is, the present invention relates to the following features. The present invention has a first aspect below.

[1] A fluorine-containing ether compound represented by Formula (1) below.

$$R^1—R^2—O—CH_2—R^3—CH_2—O—R^4—R^5 \quad (1)$$

(In Formula (1), $R^3$ is a perfluoropolyether chain, $R^2$ is represented by Formula (2) below, $R^4$ is represented by Formula (3) below, and $R^1$ and $R^5$ are hydrogen atoms or Formula (4) below.)

(2)

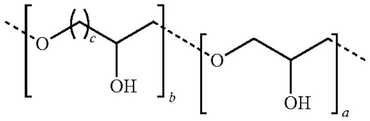

(3)

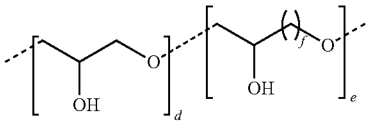

$$HO—(CH_2)_k—\quad (4)$$

(a and b in Formula (2) are an integer of 0 to 2, c in Formula (2) is an integer of 2 to 5, d and e in Formula (3) are an integer of 0 to 2, f in Formula (3) is an integer of 2 to 5, at least one of b in Formula (2) and e in Formula (3) is 1 or more, and k in Formula (4) is an integer of 3 to 6.)

The compound of the first aspect of the present invention preferably includes characteristics described in [2] to [8] below. Two or more of these characteristics are also preferably combined with each other.

[2] The fluorine-containing ether compound according to [1], in which a sum of a and b in Formula (2) above is 1 or 2.

[3] The fluorine-containing ether compound according to [1] or [2], in which $R^1—R^2—O—$ in Formula (1) above is any of Formulae (2-1) to (2-8) below.

$$R^1—O(CH_2)_2CH(OH)CH_2O—\quad (2\text{-}1)$$

$$R^1—O(CH_2)_3CH(OH)CH_2O—\quad (2\text{-}2)$$

$$R^1—O(CH_2)_4CH(OH)CH_2O—\quad (2\text{-}3)$$

$$R^1—O(CH_2)_5CH(OH)CH_2O—\quad (2\text{-}4)$$

$$R^1—O(CH_2)_2CH(OH)CH_2OCH_2CH(OH)CH_2O—\quad (2\text{-}5)$$

$$R^1—O(CH_2)_3CH(OH)CH_2OCH_2CH(OH)CH_2O—\quad (2\text{-}6)$$

$$R^1—O(CH_2)_4CH(OH)CH_2OCH_2CH(OH)CH_2O—\quad (2\text{-}7)$$

$$R^1—O(CH_2)_5CH(OH)CH_2OCH_2CH(OH)CH_2O—\quad (2\text{-}8)$$

[4] The fluorine-containing ether compound according to any one of [1] to [3], in which a sum of d and e in Formula (3) above is 1 or 2.

[5] The fluorine-containing ether compound according to any one of [1] to [4], in which $—O—R^4—R^5$ in Formula (1) above is any of Formulae (3-1) to (3-8) below.

$$—OCH_2CH(OH)(CH_2)_2O—R^5\quad (3\text{-}1)$$

$$—OCH_2CH(OH)(CH_2)_3O—R^5\quad (3\text{-}2)$$

$$—OCH_2CH(OH)(CH_2)_4O—R^5\quad (3\text{-}3)$$

$$—OCH_2CH(OH)(CH_2)_5O—R^5\quad (3\text{-}4)$$

$$—OCH_2CH(OH)CH_2OCH_2CH(OH)(CH_2)_2O—R^5\quad (3\text{-}5)$$

$$—OCH_2CH(OH)CH_2OCH_2CH(OH)(CH_2)_3O—R^5\quad (3\text{-}6)$$

$$—OCH_2CH(OH)CH_2OCH_2CH(OH)(CH_2)_4O—R^5\quad (3\text{-}7)$$

$$—OCH_2CH(OH)CH_2OCH_2CH(OH)(CH_2)_5O—R^5\quad (3\text{-}8)$$

[6] The fluorine-containing ether compound according to any one of [1] to [5], in which a total number of hydroxyl groups in $R^2$ and $R^4$ in Formula (1) above is 1 to 4.

[7] The fluorine-containing ether compound according to any one of [1] to [6], in which $R^3$ in Formula (1) above is any of Formulae (5) to (7) below.

$$—CF_2O—(CF_2CF_2O)_m—(CF_2O)_n—CF_2—\quad (5)$$

(m and n in Formula (5) indicate an average degree of polymerization and each represent 0 to 30, provided that m or n is 0.1 or more.)

$$—CF(CF_3)—(OCF(CF_3)CF_2)_g—OCF(CF_3)—\quad (6)$$

(g in Formula (6) indicates an average degree of polymerization and represents 0.1 to 30.)

$$—CF_2CF_2O—(CF_2CF_2CF_2O)_z—CF_2CF_2—\quad (7)$$

(z in Formula (7) indicates an average degree of polymerization and represents 0.1 to 30.)

[8] The fluorine-containing ether compound according to any one of [1] to [7], in which a number average molecular weight thereof is within a range of 500 to 10,000.

A second aspect of the present invention is a lubricant below.

[9] A lubricant for a magnetic recording medium including: the fluorine-containing ether compound according to any one of [1] to [8].

A third aspect of the present invention is a magnetic recording medium below.

[10] A magnetic recording medium, in which at least a magnetic layer, a protective layer, and a lubricating layer are sequentially provided on a substrate, and the lubricating layer contains the fluorine-containing ether compound according to any one of [1] to [8].

[11] The magnetic recording medium according to [10], in which an average film thickness of the lubricating layer is 0.5 nm to 2.0 nm.

Advantageous Effects of Invention

A fluorine-containing ether compound of the present invention is a compound represented by Formula (1) above. For this reason, the fluorine-containing ether compound of the present invention can be used as a material for a lubricant for a magnetic recording medium with which a lubricating layer highly effective in suppressing corrosion of a magnetic recording medium can be obtained.

Since the lubricant for a magnetic recording medium of the present invention contains the fluorine-containing ether compound of the present invention, a lubricating layer highly effective in suppressing corrosion of a magnetic recording medium can be formed.

The magnetic recording medium of the present invention has the lubricating layer containing the fluorine-containing ether compound of the present invention, and therefore has excellent corrosion resistance. For this reason, the magnetic recording medium of the present invention has excellent reliability and durability. In addition, since the magnetic recording medium of the present invention has the lubricating layer highly effective in suppressing corrosion, the thickness of a protective layer and/or the lubricating layer can be reduced.

BRIEF DESCRIPTION OF DRAWINGS

The FIGURE is a schematic cross-sectional view showing one preferred embodiment of a magnetic recording medium of the present invention.

DESCRIPTION OF EMBODIMENT

Hereinafter, preferable examples of a fluorine-containing ether compound, a lubricant for a magnetic recording medium (hereinafter, abbreviated as a "lubricant" in some cases), and a magnetic recording medium of the present invention will be described in detail. The present invention is not limited to only the embodiment shown below. For example, the present invention is not limited to only the following examples. Within the scope not departing from the gist of the present invention, numbers, quantities, ratios, compositions, types, positions, materials, configurations, and the like can be added, omitted, substituted, or changed.

[Fluorine-Containing Ether Compound]

A fluorine-containing ether compound of the present embodiment is represented by Formula (1) below.

$$R^1—R^2—O—CH_2—R^3—CH_2—O—R^4—R^5 \quad (1)$$

(In Formula (1), $R^3$ is a perfluoropolyether chain, $R^2$ is represented by Formula (2) below, $R^4$ is represented by Formula (3) below, and $R^1$ and $R^5$ are hydrogen atoms or Formula (4) below.)

(2)

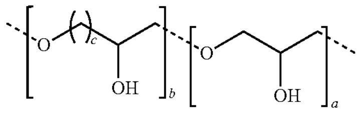

(3)

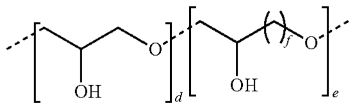

(4)

$$HO—(CH_2)_k—$$

(a and b in Formula (2) are an integer of 0 to 2, c in Formula (2) is an integer of 2 to 5, d and e in Formula (3) are an integer of 0 to 2, f in Formula (3) is an integer of 2 to 5, at least one of b in Formula (2) and e in Formula (3) is 1 or more, and k in Formula (4) is an integer of 3 to 6.)

$R^1$ and $R^5$ in Formula (1) are hydrogen atoms or Formula (4). Accordingly, the fluorine-containing ether compound represented by Formula (1) has hydroxyl groups at terminals of the chain structure. For this reason, in a case where a lubricating layer is formed on a protective layer using a lubricant containing the fluorine-containing ether compound represented by Formula (1), a suitable interaction is generated between the lubricating layer and the protective layer. Accordingly, the lubricating layer has excellent adhesion properties with respect to the protective layer.

k in Formula (4) is an integer of 3 to 6 and preferably an integer of 4 to 6. Since k in Formula (4) is 3 or more, in a case where $R^1$ and/or $R^5$ are Formula (4), a hydroxyl group is bound to three or more methylene groups linearly bound to the oxygen atom of $R^2$ or $R^4$ in $R^1$ and/or $R^5$. A lubricating layer containing a fluorine-containing ether compound in which $R^1$ and/or $R^5$ are Formula (4) has appropriate hydrophobicity due to hydrophobicity of carbon atoms contained in three or more linearly bound methylene groups in $R^1$ and/or $R^5$. As a result, the lubricating layer can prevent water from intruding into a magnetic recording medium. On the other hand, in a case where, for example, k in Formula (4) is 1 or 2, the number of methylene groups linearly bound to the oxygen atom of $R^2$ or $R^4$ is insufficient. Therefore, appropriate hydrophobicity cannot be obtained.

In addition, since k in Formula (4) is 6 or less, in a case where $R^1$ and/or $R^5$ are Formula (4), problems are not caused in adhesion properties with respect to the protective layer due to too hydrophobic $R^1$ and/or $R^5$. Therefore, the lubricating layer containing the fluorine-containing ether compound in which $R^1$ and/or $R^5$ are Formula (4) has excellent adhesion properties with respect to the protective layer, can prevent water from intruding, and is highly effective in suppressing corrosion of a magnetic recording medium.

$R^2$ in Formula (1) is a divalent linking group and represented by Formula (2). a in Formula (2) is an integer of 0 to 2, b is an integer of 0 to 2, and c is an integer of 2 to 5. In a case where a and b in Formula (2) are 0, $R^2$ is a single bond. The sum of a and b in Formula (2) (the number of hydroxyl groups in $R^2$) is 0 to 4. Since the sum of a and b is 4 or less, it is possible to prevent pickup, which is adhesion to a magnetic head as foreign matters (smears), which is caused due to excessively high polarity of the fluorine-containing ether compound in a magnetic recording medium having the lubricating layer containing the fluorine-containing ether compound.

The sum of a and b in Formula (2) (the number of hydroxyl groups in $R^2$) is preferably 1 to 3 and more preferably 1 or 2. If the sum of a and b is 1 or more, a fluorine-containing ether compound having one or more polar groups in $R^2$ is obtained. Therefore, in a case where a lubricating layer is formed on a protective layer using a lubricant containing the fluorine-containing ether compound, a suitable interaction is generated between the lubricating layer and the protective layer. As a result, the lubricating layer has favorable adhesion properties with respect to the protective layer. If the sum of a and b is 3 or less and more preferably 2 or less, hydrophilicity of the molecule is not too high, so that a fluorine-containing ether compound with moderate hydrophobicity is obtained, which is more preferable.

In a case where $R^1$ is Formula (4), the sum of a and b in Formula (2) is preferably 1. In the case where $R^1$ is Formula (4) and the sum of a and b in Formula (2) is 1, the proportion of $R^1—R^2—O—$ in the fluorine-containing ether compound represented by Formula (1) does not become too high. Accordingly, the proportion of the perfluoropolyether chain represented by $R^3$ contained in the molecule is sufficient, and a fluorine-containing ether compound with more favorable hydrophobicity is obtained.

c in Formula (2) is an integer of 2 to 5. Since c in Formula (2) is an integer of 2 to 5, in a case where b in Formula (2) is 1 or 2, $R^2$ has two or more linearly bound methylene groups ($—(CH_2)_q—$ (q in the formula is an integer of 2 to 5)). A lubricating layer containing a fluorine-containing ether compound in which b in Formula (2) is 1 or 2 has appropriate hydrophobicity due to hydrophobicity of carbon atoms contained in two or more linearly bound methylene groups in $R^2$. As a result, the lubricating layer can prevent water from intruding into a magnetic recording medium. In addition, since c in Formula (2) is 5 or less, in a case where b in Formula (2) is 1 or 2, problems are not caused in adhesion properties with respect to the protective layer due to a too hydrophobic $R^2$. Therefore, the lubricating layer containing the fluorine-containing ether compound in which b in Formula (2) is 1 or 2 has excellent adhesion properties with respect to the protective layer, can prevent water from intruding, and is more highly effective in suppressing corrosion of a magnetic recording medium.

In a case where $R^1$ is a hydrogen atom, c in Formula (2) is more preferably an integer of 3 to 5 and still more preferably 4 to 5. In a case where $R^1$ is Formula (4), c in Formula (2) is more preferably an integer of 2 to 3.

In a case where b in Formula (2) is 0, $R^1$ is preferably Formula (4) to obtain a fluorine-containing ether compound having more appropriate hydrophobicity.

$[O(CH_2)_cCH(OH)CH_2]b$ in Formula (2) is placed closer to the $R^1$ side than $[OCH_2CH(OH)CH_2]_a$. For this reason, a fluorine-containing ether compound capable of forming a lubricating layer highly effective in suppressing corrosion of a magnetic recording medium can be obtained compared to a case where, for example, $[OCH_2CH(OH)CH_2]_a$ is placed closer to the $R^1$ side than $[O(CH_2)_cCH(OH)CH_2]b$. It is inferred that this is due to the following reasons.

For example, in the case where $[OCH_2CH(OH)CH_2]_a$ is placed closer to the $R^1$ side than $[O(CH_2)_cCH(OH)CH_2]_b$, $[OCH_2CH(OH)CH_2]_a$ forms a structure in which a carbon atom to which a hydroxyl group is bound is placed between methylene groups to which an oxygen atom is bound. Since this structure is highly flexible, $R^2$ is highly flexible. This facilitates aggregation of $R^1$—$R^2$ in a fluorine-containing ether compound contained in a lubricating layer formed on a protective layer. As a result, it is inferred that the hydrophobic parts (two or more linearly bound methylene groups) contained in $[O(CH_2)_cCH(OH)CH_2]_b$ in the lubricating layer may be less likely to be arranged facing the surface on a side opposite to the protective layer, resulting in insufficient hydrophobicity of the lubricating layer and insufficient effect of suppressing corrosion of a magnetic recording medium.

On the other hand, in the case where $[O(CH_2)_cCH(OH)CH_2]_b$ is placed closer to the $R^1$ side than $[OCH_2CH(OH)CH_2]_a$, even if flexibility is imparted by $[OCH_2CH(OH)CH_2]_a$, the flexibility of only the part in $R^2$ which is placed closer to the perfluoropolyether chain represented by $R^3$ increases, and the influence on the flexibility of $R^1$—$R^2$ is small. For this reason, it is inferred that the influence on the arrangement of the hydrophobic parts in $[O(CH_2)_cCH(OH)CH_2]_b$ in the lubricating layer may also be small, and sufficient hydrophobicity of the lubricating layer may be ensured.

In the fluorine-containing ether compound represented by Formula (1), $R^1$—$R^2$—O— in Formula (1) can be appropriately selected depending on the performance required of a lubricant containing the fluorine-containing ether compound. $R^1$—$R^2$—O— in Formula (1) is preferably any of Formulae (2-1) to (2-8) below.

$$R^1\text{—}O(CH_2)_2CH(OH)CH_2O\text{—} \quad (2\text{-}1)$$

$$R^1\text{—}O(CH_2)_3CH(OH)CH_2O\text{—} \quad (2\text{-}2)$$

$$R^1\text{—}O(CH_2)_4CH(OH)CH_2O\text{—} \quad (2\text{-}3)$$

$$R^1\text{—}O(CH_2)_5CH(OH)CH_2O\text{—} \quad (2\text{-}4)$$

$$R^1\text{—}O(CH_2)_2CH(OH)CH_2OCH_2CH(OH)CH_2O\text{—} \quad (2\text{-}5)$$

$$R^1\text{—}O(CH_2)_3CH(OH)CH_2OCH_2CH(OH)CH_2O\text{—} \quad (2\text{-}6)$$

$$R^1\text{—}O(CH_2)_4CH(OH)CH_2OCH_2CH(OH)CH_2O\text{—} \quad (2\text{-}7)$$

$$R^1\text{—}O(CH_2)_5CH(OH)CH_2OCH_2CH(OH)CH_2O\text{—} \quad (2\text{-}8)$$

a, b, and c when the structures of Formulae (2-1) to (2-8) are adapted to Formula (2) are as follows.

Formula (2-1): a=0, b=1, c=2

Formula (2-2): a=0, b=1, c=3

Formula (2-3): a=0, b=1, c=4

Formula (2-4): a=0, b=1, c=5

Formula (2-5): a=1, b=1, c=2

Formula (2-6): a=1, b=1, c=3

Formula (2-7): a=1, b=1, c=4

Formula (2-8): a=1, b=1, c=5

$R^4$ in Formula (1) is a divalent linking group and represented by Formula (3). d in Formula (3) is an integer of 0 to 2, e is an integer of 0 to 2, and f is an integer of 2 to 5. In a case where d and e in Formula (3) are 0, $R^4$ is a single bond. The sum of d and e in Formula (3) (the number of hydroxyl groups in $R^4$) is 0 to 4. Since the sum of d and e is 4 or less, it is possible to prevent pickup, which is adhesion to a magnetic head as foreign matters (smears), which is caused due to excessively high polarity of the fluorine-containing ether compound in a magnetic recording medium having the lubricating layer containing the fluorine-containing ether compound.

The sum of d and e in Formula (3) (the number of hydroxyl groups in $R^4$) is preferably 1 to 3 and more preferably 1 or 2. If the sum of d and e is 1 or more, a fluorine-containing ether compound having one or more polar groups in $R^4$ is obtained. Therefore, in a case where a lubricating layer is formed on a protective layer using a lubricant containing the fluorine-containing ether compound, a suitable interaction is generated between the lubricating layer and the protective layer. As a result, the lubricating layer has favorable adhesion properties with respect to the protective layer. If the sum of d and e is 3 or less and more preferably 2 or less, hydrophilicity of the molecule is not too high, so that a fluorine-containing ether compound with moderate hydrophobicity is obtained, which is more preferable.

In a case where $R^5$ is Formula (4), the sum of d and e in Formula (3) is preferably 1. In the case where $R^5$ is Formula (4) and the sum of d and e in Formula (3) is 1, the proportion of —O—$R^4$—$R^5$ in the fluorine-containing ether compound represented by Formula (1) does not become too high. Accordingly, the proportion of the perfluoropolyether chain represented by $R^3$ contained in the molecule is sufficient, and a fluorine-containing ether compound with more favorable hydrophobicity is obtained.

f in Formula (3) is an integer of 2 to 5. Since f in Formula (3) is an integer of 2 to 5, in a case where e in Formula (3) is 1 or 2, $R^4$ has two or more linearly bound methylene groups (—$(CH_2)_q$— (q in the formula is an integer of 2 to 5)). A lubricating layer containing a fluorine-containing ether compound in which e in Formula (3) is 1 or 2 has appropriate hydrophobicity due to hydrophobicity of carbon atoms contained in two or more linearly bound methylene groups in $R^4$. As a result, the lubricating layer can prevent water from intruding into a magnetic recording medium. In addition, since f in Formula (3) is 5 or less, in a case where e in Formula (3) is 1 or 2, problems are not caused in adhesion properties with respect to the protective layer due to a too hydrophobic $R^4$. Therefore, the lubricating layer containing the fluorine-containing ether compound in which e in Formula (3) is 1 or 2 has excellent adhesion properties with respect to the protective layer, can prevent water from intruding, and is more highly effective in suppressing corrosion of a magnetic recording medium.

In a case where $R^5$ is a hydrogen atom, f in Formula (3) is more preferably an integer of 3 to 5 and still more preferably 4 to 5. In a case where $R^5$ is Formula (4), f in Formula (3) is more preferably an integer of 2 to 3.

In a case where e in Formula (3) is 0, $R^5$ is preferably Formula (4) to obtain a fluorine-containing ether compound having more appropriate hydrophobicity.

$[CH_2CH(OH)(CH_2)_fO]_e$ in Formula (3) is placed closer to the $R^5$ side than $[CH_2CH(OH)CH_2O]_d$. For this reason, a fluorine-containing ether compound capable of forming a lubricating layer highly effective in suppressing corrosion of a magnetic recording medium can be obtained compared to a case where, for example, $[CH_2CH(OH)CH_2O]_d$ is placed closer to the $R^5$ side than $[CH_2CH(OH)(CH_2)_fO]_e$. It is inferred that this is due to the following reasons.

For example, in the case where $[CH_2CH(OH)CH_2O]_d$ is placed closer to the $R^5$ side than $[CH_2CH(OH)(CH_2)_fO]_e$, a structure is formed in which a carbon atom to which a hydroxyl group is bound is placed between methylene groups to which an oxygen atom is bound. Since this structure is highly flexible, $R^4$ is highly flexible. This facilitates aggregation of $R^4$-$R^5$ in a fluorine-containing ether compound contained in a lubricating layer formed on a protective layer. As a result, it is inferred that the hydrophobic parts (two or more linearly bound methylene groups) contained in $[CH_2CH(OH)(CH_2)_fO]_e$ in the lubricating layer may be less likely to be arranged facing the surface on a side opposite to the protective layer, resulting in insufficient hydrophobicity of the lubricating layer and insufficient effect of suppressing corrosion of a magnetic recording medium.

On the other hand, in the case where $[CH_2CH(OH)(CH_2)_fO]_e$ is placed closer to the $R^5$ side than $[CH_2CH(OH)CH_2O]_d$, even if flexibility is imparted by $[CH_2CH(OH)CH_2O]_d$, the influence on the flexibility of $R^4$—$R^5$ is small. For this reason, it is inferred that the influence on the arrangement of the hydrophobic parts in $[CH_2CH(OH)(CH_2)_fO]_e$ in the lubricating layer may also be small, and sufficient hydrophobicity of the lubricating layer may be ensured.

In the fluorine-containing ether compound represented by Formula (1), —O—$R^4$—$R^5$ in Formula (1) can be appropriately selected depending on the performance and the like required of a lubricant containing the fluorine-containing ether compound. —O—$R^4$—$R^5$ in Formula (1) is preferably any of Formulae (3-1) to (3-8) below.

$$OCH_2CH(OH)(CH_2)_2O—R^5 \quad (3\text{-}1)$$

$$—OCH_2CH(OH)(CH_2)_3O—R^5 \quad (3\text{-}2)$$

$$—OCH_2CH(OH)(CH_2)_4O—R^5 \quad (3\text{-}3)$$

$$—OCH_2CH(OH)(CH_2)_5O—R^5 \quad (3\text{-}4)$$

$$—OCH_2CH(OH)CH_2OCH_2CH(OH)(CH_2)_2O—R^5 \quad (3\text{-}5)$$

$$—OCH_2CH(OH)CH_2OCH_2CH(OH)(CH_2)_3O—R^5 \quad (3\text{-}6)$$

$$—OCH_2CH(OH)CH_2OCH_2CH(OH)(CH_2)_4O—R^5 \quad (3\text{-}7)$$

$$—OCH_2CH(OH)CH_2OCH_2CH(OH)(CH_2)_5O—R^5 \quad (3\text{-}8)$$

d, e, and f when the structures of Formulae (3-1) to (3-8) are adapted to Formula (3) are as follows.

Formula (3-1): d=0, e=1, f=2
Formula (3-2): d=0, e=1, f=3
Formula (3-3): d=0, e=1, f=4
Formula (3-4): d=0, e=1, f=5
Formula (3-5): d=1, e=1, f=2
Formula (3-6): d=1, e=1, f=3
Formula (3-7): d=1, e=1, f=4
Formula (3-8): d=1, e=1, f=5

In the fluorine-containing ether compound represented by Formula (1), $R^2$ and $R^4$ each contain 0 to 4 hydroxyl groups. Since at least one of b in Formula (2) and e in Formula (3) is 1 or more, the total number of hydroxyl groups in $R^2$ and hydroxyl groups in $R^4$ is 1 to 8. In the fluorine-containing ether compound represented by Formula (1), since the total number of hydroxyl groups in $R^2$ and $R^4$ are 1 or more, in a case where a lubricating layer is formed on a protective layer using a lubricant containing the fluorine-containing ether compound, a lubricating layer having excellent adhesion properties with respect to a protective layer can be obtained. Since the total number of hydroxyl groups in $R^2$ and $R^4$ are 8 or less, it is possible to prevent pickup, which is adhesion to a magnetic head as foreign matters (smears) due to excessively high polarity of the fluorine-containing ether compound. The total number of hydroxyl groups in $R^2$ and $R^4$ is preferably 1 to 4 and more preferably 2 to 3.

In the fluorine-containing ether compound represented by Formula (1), $R^1$—$R^2$—O— and —O—$R^4$—$R^5$ may be the same as or different from each other. In a case where $R^1$—$R^2$—O— and —O—$R^4$—$R^5$ are the same as each other, a fluorine-containing ether compound which is likely to wet and spread evenly on the protective layer, and from which a lubricating layer having a uniform film thickness is likely to be obtained, is obtained. As a result, the lubricating layer containing this fluorine-containing ether compound is likely to have a favorable coating rate, which is preferable. In addition, in the case where $R^1$—$R^2$—O— and —O—$R^4$—$R^5$ are the same as each other, the compound can be efficiently produced through fewer production steps compared to a case where $R^1$—$R^2$—O— and —O—$R^4$—$R^5$ are different from each other.

$R^3$ in the fluorine-containing ether compound represented by Formula (1) is a perfluoropolyether chain (PFPE chain). Due to the PFPE chain represented by $R^3$, in a case where a lubricant containing the fluorine-containing ether compound of the present embodiment is applied onto a protective layer to form a lubricating layer, the surface of the protective layer is covered. In addition, lubricity is imparted to the lubricating layer to reduce frictional force between a magnetic head and the protective layer. Furthermore, since the PFPE chain has low surface energy, water resistance is imparted to the lubricating layer containing the fluorine-containing ether compound of the present embodiment and the corrosion resistance of the magnetic recording medium on which the lubricating layer is provided is improved.

$R^3$ is a PFPE chain and can be appropriately selected depending on the performance and the like required of a lubricant containing a fluorine-containing ether compound. Examples of PFPE chains include PFPE chains consisting of a perfluoromethylene oxide polymer, a perfluoroethylene oxide polymer, a perfluoro-n-propylene oxide polymer, a perfluoroisopropylene oxide polymer, and copolymers thereof.

Specifically, $R^3$ in Formula (1) is preferably any of Formulae (5) to (7) below. The arrangement sequence of $(CF_2CF_2O)$ and $(CF_2O)$ which are repeating units in Formula (5) is not particularly limited. Formula (5) may include any of a random copolymer, a block copolymer, and an alternating copolymer composed of the monomer units $(CF_2—CF_2—O)$ and $(CF_2—O)$.

$$CF_2O—(CF_2CF_2O)_m—(CF_2O)_n—CF_2— \quad (5)$$

(m and n in Formula (5) indicate an average degree of polymerization and each represent 0 to 30, provided that m or n is 0.1 or more.)

$$—CF(CF_3)—(OCF(CF_3)CF_2)_g—OCF(CF_3)— \quad (6)$$

(g in Formula (6) indicates an average degree of polymerization and represents 0.1 to 30.)

$$—CF_2CF_2O—(CF_2CF_2CF_2O)_z—CF_2CF_2— \quad (7)$$

(z in Formula (7) indicates an average degree of polymerization and represents 0.1 to 30.)

m and n indicating an average degree of polymerization in Formula (5) are each 0 to 30 (provided that m or n is 0.1 or more), g indicating an average degree of polymerization in Formula (6) is 0.1 to 30, and z indicating an average degree of polymerization in Formula (7) is 0.1 to 30. If m, n, g, and z are 0.1 or more, a fluorine-containing ether compound, from which a lubricating layer having favorable wear resistance and capable of further suppressing corrosion of a magnetic recording medium can be obtained, is obtained. In addition, if m, n, g, and z are each 30 or less, the viscosity of a fluorine-containing ether compound does not become too high, and a lubricant containing this fluorine-containing ether compound becomes easy to apply, which is preferable. All of m, n, g, and z indicating an average degree of polymerization are preferably 2 to 20 and more preferably 3 to 8, to obtain a fluorine-containing ether compound which can easily wet and spread on a protective layer and from which a lubricating layer having a uniform film thickness is likely to be obtained. m, n, g, and z each may be, as necessary, 0.1 to 25, 0.5 to 18, 1 to 15, 5 to 10, 3 to 10, 3 to 6, or the like.

In the case where $R^3$ in Formula (1) is any of Formulae (5) to (7), a fluorine-containing ether compound is easily synthesized, which is preferable. In a case where $R^3$ is Formula (5) or (7), the procurement of raw materials is easy, which is more preferable.

In addition, in the case where $R^3$ is any of Formulae (5) to (7), the ratio of the number of oxygen atoms (the number of ether bonds (—O—)) to the number of carbon atoms in the perfluoropolyether chain is appropriate. For this reason, a fluorine-containing ether compound with moderate hardness is obtained. Accordingly, a fluorine-containing ether compound applied onto a protective layer is less likely to be aggregated on the protective layer, and a lubricating layer having an even thinner thickness at a sufficient coating rate can be formed.

In particular, in a case where $R^3$ in Formula (1) is Formula (7) having a repeating unit containing three linearly bound $—CF_2—$, the lubricating layer containing a fluorine-containing ether compound more effectively suppresses corrosion of a magnetic recording medium due to excellent hydrophobicity of the PFPE chain.

It is preferable that the fluorine-containing ether compound represented by Formula (1) be specifically any compound represented by Formulae (1A) to (1P), (2A) to (2P), and (3A) to (3P). Repeating numbers za to zp in Formulae (1A) to (1P), repeating numbers ya to yp in Formulae (2A) to (2P), and repeating numbers ma to mp and na to np in (3A) to (3P) are values indicating an average degree of polymerization, and are not necessarily integers.

In the compound represented by Formula (1A), $R^1$ is a hydrogen atom, and $R^2$ is Formula (2) in which a=0, b=1, and c=2. $R^3$ is Formula (7), $R^4$ is Formula (3) in which d=0, e=1, and f=2, and $R^5$ is a hydrogen atom.

In the compound represented by Formula (1B), $R^1$ is a hydrogen atom, and $R^2$ is Formula (2) in which a=0, b=1, and c=3. $R^3$ is Formula (7), $R^4$ is Formula (3) in which d=0, e=1, and f=3, and $R^5$ is a hydrogen atom.

In the compound represented by Formula (1C), $R^1$ is a hydrogen atom, and $R^2$ is Formula (2) in which a=0, b=1, and c=4. $R^3$ is Formula (7), $R^4$ is Formula (3) in which d=0, e=1, and f=4, and $R^5$ is a hydrogen atom.

In the compound represented by Formula (1D), $R^1$ is a hydrogen atom, and $R^2$ is Formula (2) in which a=0, b=1, and c=5. $R^3$ is Formula (7), $R^4$ is Formula (3) in which d=0, e=1, and f=5, and $R^5$ is a hydrogen atom.

In the compound represented by Formula (1E), $R^1$ is a hydrogen atom, and $R^2$ is Formula (2) in which a=0, b=1, and c=2. $R^3$ is Formula (7), $R^4$ is Formula (3) in which d=1, e=1, and f=2, and $R^5$ is a hydrogen atom.

In the compound represented by Formula (1F), $R^1$ is a hydrogen atom, and $R^2$ is Formula (2) in which a=0, b=1, and c=4. $R^3$ is Formula (7), $R^4$ is Formula (3) in which d=1, e=1, and f=2, and $R^5$ is a hydrogen atom.

In the compound represented by Formula (1G), $R^1$ is a hydrogen atom, and $R^2$ is Formula (2) in which a=0, b=1, and c=5. $R^3$ is Formula (7), $R^4$ is Formula (3) in which d=1, e=1, and f=2, and $R^5$ is a hydrogen atom.

In the compound represented by Formula (1H), $R^1$ is a hydrogen atom, and $R^2$ is Formula (2) in which a=0, b=1, and c=4. $R^3$ is Formula (7), $R^4$ is Formula (3) in which d=1, e=1, and f=4, and $R^5$ is a hydrogen atom.

In the compound represented by Formula (1I), $R^1$ is a hydrogen atom, and $R^2$ is Formula (2) in which a=1, b=1, and c=2. $R^3$ is Formula (7), $R^4$ is Formula (3) in which d=1, e=1, and f=2, and $R^5$ is a hydrogen atom.

In the compound represented by Formula (1J), $R^1$ is Formula (4) in which k=3. $R^2$ is Formula (2) in which a=1 and b=0. $R^3$ is Formula (7), $R^4$ is Formula (3) in which d=0, e=1, and f=4. $R^5$ is a hydrogen atom.

In the compound represented by Formula (1K), $R^1$ is Formula (4) in which k=3. $R^2$ is Formula (2) in which a=1 and b=0. $R^3$ is Formula (7), $R^4$ is Formula (3) in which d=1, e=1, and f=2. $R^5$ is a hydrogen atom.

In the compound represented by Formula (1L), $R^1$ is Formula (4) in which k=3. $R^2$ is Formula (2) in which a=0, b=1, and c=2. $R^3$ is Formula (7), $R^4$ is Formula (3) in which d=0, e=1, and f=2. $R^5$ is Formula (4) in which k=3.

In the compound represented by Formula (1M), $R^1$ is Formula (4) in which k=3. $R^2$ is Formula (2) in which a=0, b=1, and c=2. $R^3$ is Formula (7), $R^4$ is Formula (3) in which d=1, e=1, and f=2. $R^5$ is a hydrogen atom.

In the compound represented by Formula (1N), $R^1$ is Formula (4) in which k=3. $R^2$ is Formula (2) in which a=0, b=1, and c=3. $R^3$ is Formula (7), $R^4$ is Formula (3) in which d=1, e=1, and f=2. $R^5$ is a hydrogen atom.

In the compound represented by Formula (1P), $R^1$ is Formula (4) in which k=6. $R^2$ is Formula (2) in which a=0, b=1, and c=2. $R^3$ is Formula (7), $R^4$ is Formula (3) in which d=1, e=1, and f=2. $R^5$ is a hydrogen atom.

In the compound represented by Formula (2A), $R^1$ is a hydrogen atom, and $R^2$ is Formula (2) in which a=0, b=1, and c=2. $R^3$ is Formula (5) in which n=0. $R^4$ is Formula (3) in which d=0, e=1, and f=2. $R^5$ is a hydrogen atom.

In the compound represented by Formula (2B), $R^1$ is a hydrogen atom, and $R^2$ is Formula (2) in which a=0, b=1, and c=3. $R^3$ is Formula (5) in which n=0. $R^4$ is Formula (3) in which d=0, e=1, and f=3, and $R^5$ is a hydrogen atom.

In the compound represented by Formula (2C), $R^1$ is a hydrogen atom, and $R^2$ is Formula (2) in which a=0, b=1, and c=4. $R^3$ is Formula (5) in which n=0. $R^4$ is Formula (3) in which d=0, e=1, and f=4, and $R^5$ is a hydrogen atom.

In the compound represented by Formula (2D), $R^1$ is a hydrogen atom, and $R^2$ is Formula (2) in which a=0, b=1, and c=5. $R^3$ is Formula (5) in which n=0. $R^4$ is Formula (3) in which d=0, e=1, and f=5, and $R^5$ is a hydrogen atom.

In the compound represented by Formula (2E), $R^1$ is a hydrogen atom, and $R^2$ is Formula (2) in which a=0, b=1, and c=2. $R^3$ is Formula (5) in which n=0. $R^4$ is Formula (3) in which d=1, e=1, and f=2, and $R^5$ is a hydrogen atom.

In the compound represented by Formula (2F), $R^1$ is a hydrogen atom, and $R^2$ is Formula (2) in which a=0, b=1, and c=4. $R^3$ is Formula (5) in which n=0. $R^4$ is Formula (3) in which d=1, e=1, and f=2, and $R^5$ is a hydrogen atom.

In the compound represented by Formula (2G), $R^1$ is a hydrogen atom, and $R^2$ is Formula (2) in which a=0, b=1, and c=5. $R^3$ is Formula (5) in which n=0. $R^4$ is Formula (3) in which d=1, e=1, and f=2, and $R^5$ is a hydrogen atom.

In the compound represented by Formula (2H), $R^1$ is a hydrogen atom, and $R^2$ is Formula (2) in which a=0, b=1, and c=4. $R^3$ is Formula (5) in which n=0. $R^4$ is Formula (3) in which d=1, e=1, and f=4, and $R^5$ is a hydrogen atom.

In the compound represented by Formula (2I), $R^1$ is a hydrogen atom, and $R^2$ is Formula (2) in which a=1, b=1, and c=2. $R^3$ is Formula (5) in which n=0. $R^4$ is Formula (3) in which d=1, e=1, and f=2, and $R^5$ is a hydrogen atom.

In the compound represented by Formula (2J), $R^1$ is Formula (4) in which k=3. $R^2$ is Formula (2) in which a=1 and b=0. $R^3$ is Formula (5) in which n=0. $R^4$ is Formula (3) in which d=0, e=1, and f=4. $R^5$ is a hydrogen atom.

In the compound represented by Formula (2K), $R^1$ is Formula (4) in which k=3. $R^2$ is Formula (2) in which a=1 and b=0. $R^3$ is Formula (5) in which n=0. $R^4$ is Formula (3) in which d=1, e=1, and f=2. $R^5$ is a hydrogen atom.

In the compound represented by Formula (2L), $R^1$ is Formula (4) in which k=3. $R^2$ is Formula (2) in which a=0, b=1, and c=2. $R^3$ is Formula (5) in which n=0. $R^4$ is Formula (3) in which d=0, e=1, and f=2. $R^5$ is Formula (4) in which k=3.

In the compound represented by Formula (2M), $R^1$ is Formula (4) in which k=3. $R^2$ is Formula (2) in which a=0, b=1, and c=2. $R^3$ is Formula (5) in which n=0. $R^4$ is Formula (3) in which d=1, e=1, and f=2. $R^5$ is a hydrogen atom.

In the compound represented by Formula (2N), $R^1$ is Formula (4) in which k=3. $R^2$ is Formula (2) in which a=0, b=1, and c=3. $R^3$ is Formula (5) in which n=0. $R^4$ is Formula (3) in which d=1, e=1, and f=2. $R^5$ is a hydrogen atom.

In the compound represented by Formula (2P), $R^1$ is Formula (4) in which k=6. $R^2$ is Formula (2) in which a=0, b=1, and c=2. $R^3$ is Formula (5) in which n=0. $R^4$ is Formula (3) in which d=1, e=1, and f=2. $R^5$ is a hydrogen atom.

In the compound represented by Formula (3A), $R^1$ is a hydrogen atom, and $R^2$ is Formula (2) in which a=0, b=1, and c=2. $R^3$ is Formula (5), $R^4$ is Formula (3) in which d=0, e=1, and f=2, and $R^5$ is a hydrogen atom.

In the compound represented by Formula (3B), $R^1$ is a hydrogen atom, and $R^2$ is Formula (2) in which a=0, b=1, and c=3. $R^3$ is Formula (5), $R^4$ is Formula (3) in which d=0, e=1, and f=3, and $R^5$ is a hydrogen atom.

In the compound represented by Formula (3C), $R^1$ is a hydrogen atom, and $R^2$ is Formula (2) in which a=0, b=1, and c=4. $R^3$ is Formula (5), $R^4$ is Formula (3) in which d=0, e=1, and f=4, and $R^5$ is a hydrogen atom.

In the compound represented by Formula (3D), $R^1$ is a hydrogen atom, and $R^2$ is Formula (2) in which a=0, b=1, and c=5. $R^3$ is Formula (5), $R^4$ is Formula (3) in which d=0, e=1, and f=5, and $R^5$ is a hydrogen atom.

In the compound represented by Formula (3E), $R^1$ is a hydrogen atom, and $R^2$ is Formula (2) in which a=0, b=1, and c=2. $R^3$ is Formula (5), $R^4$ is Formula (3) in which d=1, e=1, and f=2, and $R^5$ is a hydrogen atom.

In the compound represented by Formula (3F), $R^1$ is a hydrogen atom, and $R^2$ is Formula (2) in which a=0, b=1, and c=4. $R^3$ is Formula (5), $R^4$ is Formula (3) in which d=1, e=1, and f=2, and $R^5$ is a hydrogen atom.

In the compound represented by Formula (3G), $R^1$ is a hydrogen atom, and $R^2$ is Formula (2) in which a=0, b=1, and c=5. $R^3$ is Formula (5), $R^4$ is Formula (3) in which d=1, e=1, and f=2, and $R^5$ is a hydrogen atom.

In the compound represented by Formula (311), $R^1$ is a hydrogen atom, and $R^2$ is Formula (2) in which a=0, b=1, and c=4. $R^3$ is Formula (5), $R^4$ is Formula (3) in which d=1, e=1, and f=4, and $R^5$ is a hydrogen atom.

In the compound represented by Formula (3I), $R^1$ is a hydrogen atom, and $R^2$ is Formula (2) in which a=1, b=1, and c=2. $R^3$ is Formula (5), $R^4$ is Formula (3) in which d=1, e=1, and f=2, and $R^5$ is a hydrogen atom.

In the compound represented by Formula (3J), $R^1$ is Formula (4) in which k=3. $R^2$ is Formula (2) in which a=1 and b=0. $R^3$ is Formula (5), $R^4$ is Formula (3) in which d=0, e=1, and f=4. $R^5$ is a hydrogen atom.

In the compound represented by Formula (3K), $R^1$ is Formula (4) in which k=3. $R^2$ is Formula (2) in which a=1 and b=0. $R^3$ is Formula (5), $R^4$ is Formula (3) in which d=1, e=1, and f=2. $R^5$ is a hydrogen atom.

In the compound represented by Formula (3L), $R^1$ is Formula (4) in which k=3. $R^2$ is Formula (2) in which a=0, b=1, and c=2. $R^3$ is Formula (5), $R^4$ is Formula (3) in which d=0, e=1, and f=2. $R^5$ is Formula (4) in which k=3.

In the compound represented by Formula (3M), $R^1$ is Formula (4) in which k=3. $R^2$ is Formula (2) in which a=0, b=1, and c=2. $R^3$ is Formula (5), $R^4$ is Formula (3) in which d=1, e=1, and f=2. $R^5$ is a hydrogen atom.

In the compound represented by Formula (3N), $R^1$ is Formula (4) in which k=3. $R^2$ is Formula (2) in which a=0, b=1, and c=3. $R^3$ is Formula (5), $R^4$ is Formula (3) in which d=1, e=1, and f=2. $R^5$ is a hydrogen atom.

In the compound represented by Formula (3P), $R^1$ is Formula (4) in which k=6. $R^2$ is Formula (2) in which a=0, b=1, and c=2. $R^3$ is Formula (5), $R^4$ is Formula (3) in which d=1, e=1, and f=2. $R^5$ is a hydrogen atom.

(1A)

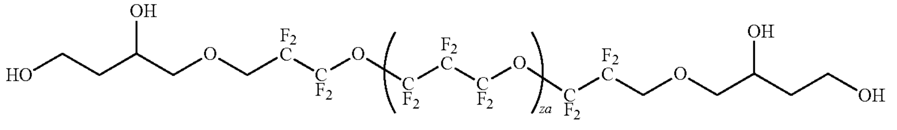

(1B)

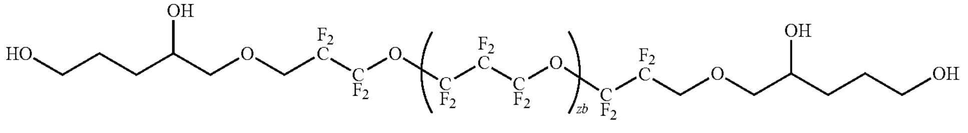

-continued (1C)

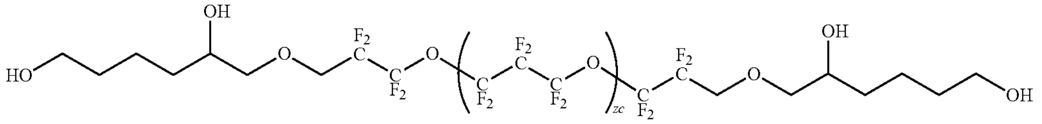

(1D)

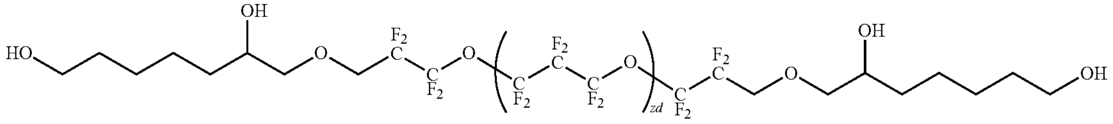

(1E)

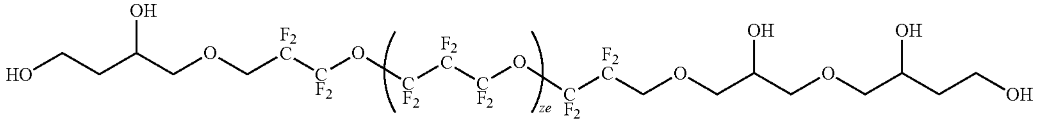

(1F)

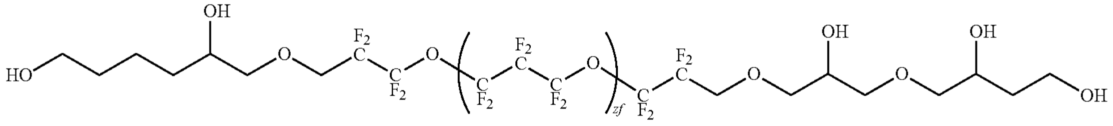

(1G)

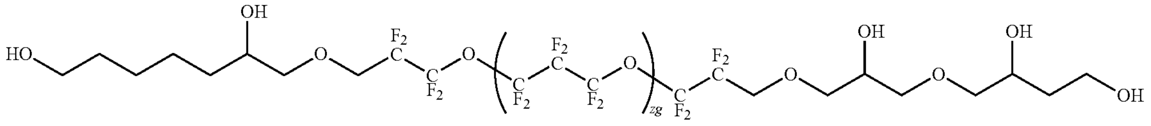

(za in Formula (1A) indicates an average degree of polymerization and represents 0.1 to 30.)

(zb in Formula (1B) indicates an average degree of polymerization and represents 0.1 to 30.)

(ze in Formula (1C) indicates an average degree of polymerization and represents 0.1 to 30.)

(zd in Formula (1D) indicates an average degree of polymerization and represents 0.1 to 30.)

(ze in Formula (1E) indicates an average degree of polymerization and represents 0.1 to 30.)

(zf in Formula (1F) indicates an average degree of polymerization and represents 0.1 to 30.)

(zg in Formula (1G) indicates an average degree of polymerization and represents 0.1 to 30.)

(1H)

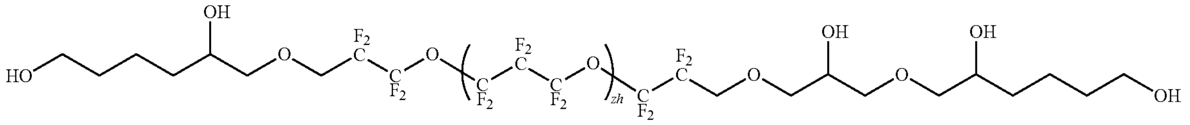

(1I)

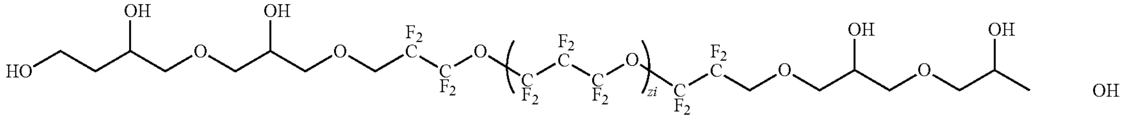

(1J)

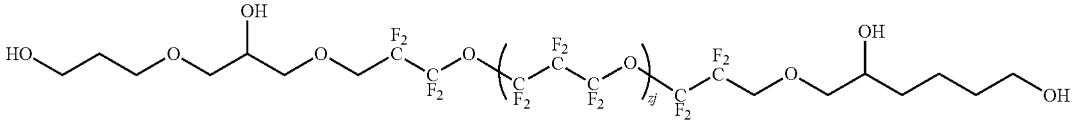

(1K)

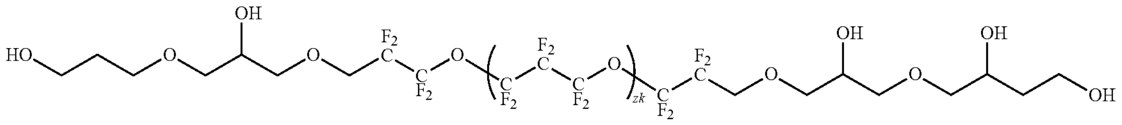

-continued (1L)

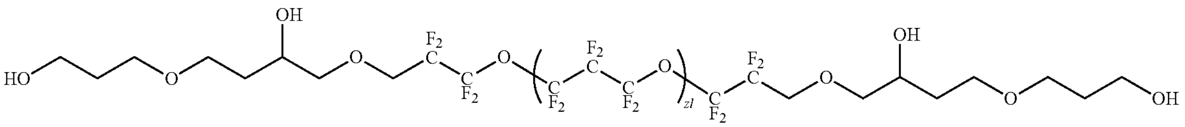

(1M)

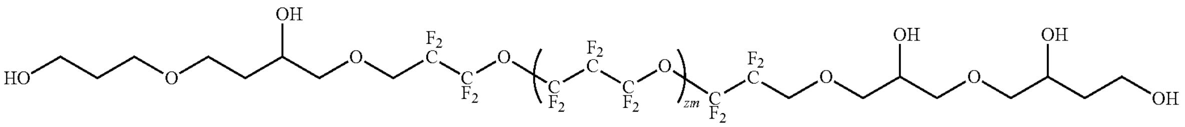

(1N)

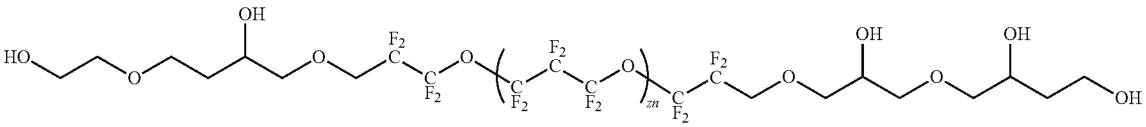

(1P)

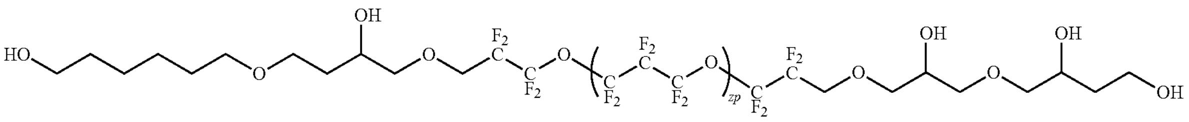

(zh in Formula (1H) indicates an average degree of polymerization and represents 0.1 to 30.)

(zi in Formula (1I) indicates an average degree of polymerization and represents 0.1 to 30.)

(zj in Formula (1J) indicates an average degree of polymerization and represents 0.1 to 30.)

(zk in Formula (1K) indicates an average degree of polymerization and represents 0.1 to 30.)

(zl in Formula (1L) indicates an average degree of polymerization and represents 0.1 to 30.)

(zm in Formula (1M) indicates an average degree of polymerization and represents 0.1 to 30.)

(zn in Formula (1N) indicates an average degree of polymerization and represents 0.1 to 30.)

(zp in Formula (1P) indicates an average degree of polymerization and represents 0.1 to 30.)

(2A)

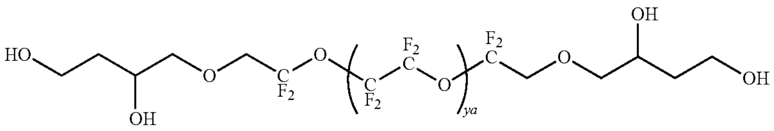

(2B)

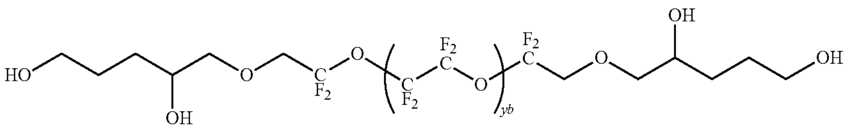

(2C)

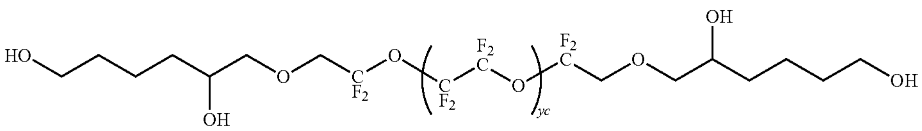

(2D)

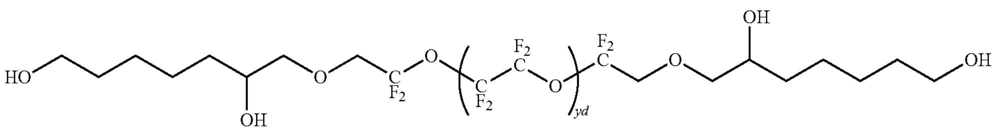

(2E)

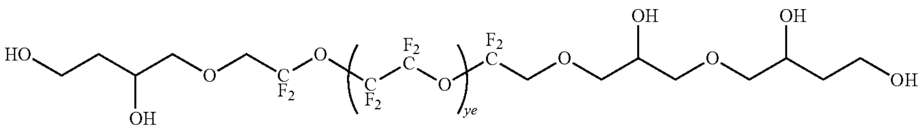

-continued (2F)

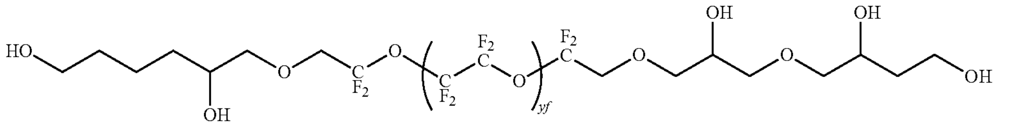

(2G)

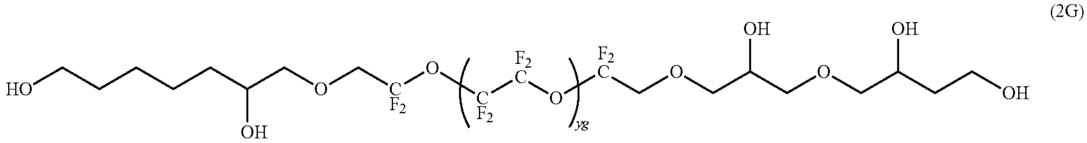

(ya in Formula (2A) indicates an average degree of polymerization and represents 0.1 to 30.)

(yb in Formula (2B) indicates an average degree of polymerization and represents 0.1 to 30.)

(yc in Formula (2C) indicates an average degree of polymerization and represents 0.1 to 30.)

(yd in Formula (2D) indicates an average degree of polymerization and represents 0.1 to 30.)

(ye in Formula (2E) indicates an average degree of polymerization and represents 0.1 to 30.)

(yf in Formula (2F) indicates an average degree of polymerization and represents 0.1 to 30.)

(yg in Formula (2G) indicates an average degree of polymerization and represents 0.1 to 30.)

(2H)

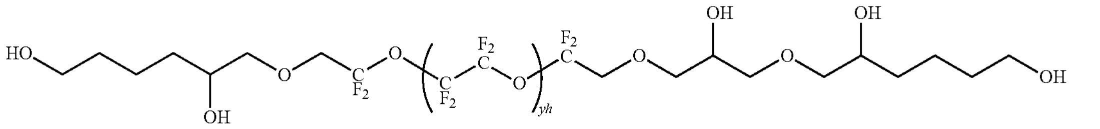

(2I)

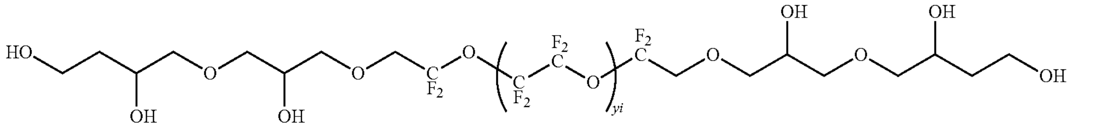

(2J)

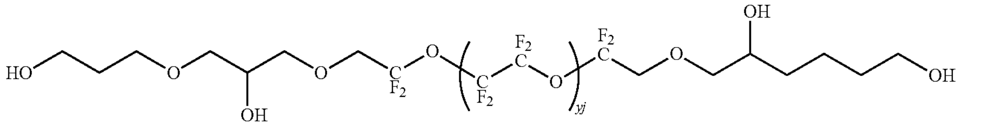

(2K)

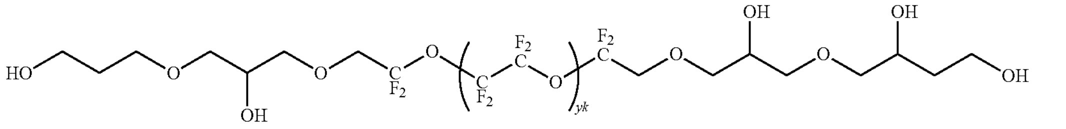

(2L)

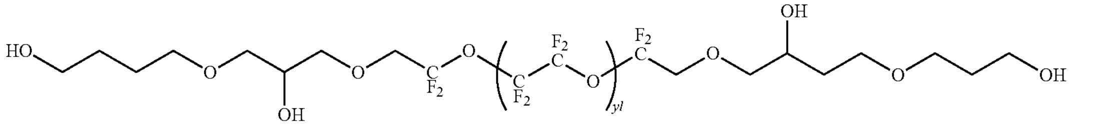

(2M)

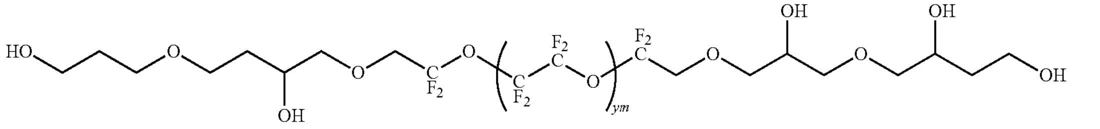

(2N)

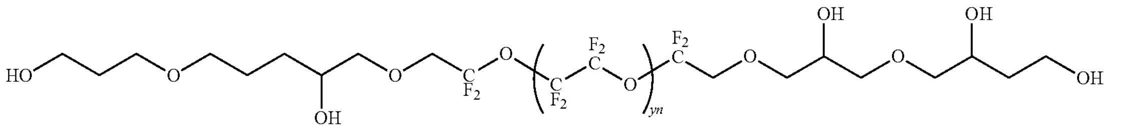

-continued (2P)

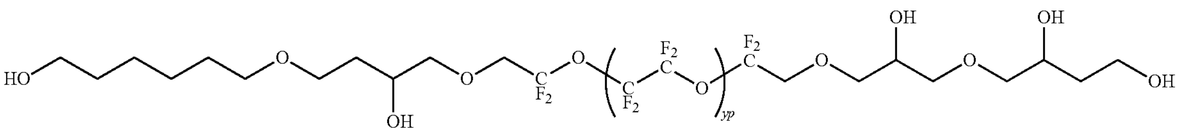

(yh in Formula (2H) indicates an average degree of polymerization and represents 0.1 to 30.)

(yi in Formula (2I) indicates an average degree of polymerization and represents 0.1 to 30.)

(yj in Formula (2J) indicates an average degree of polymerization and represents 0.1 to 30.)

(ym in Formula (2M) indicates an average degree of polymerization and represents 0.1 to 30.)

(yn in Formula (2N) indicates an average degree of polymerization and represents 0.1 to 30.)

(yp in Formula (2P) indicates an average degree of polymerization and represents 0.1 to 30.)

(3A)

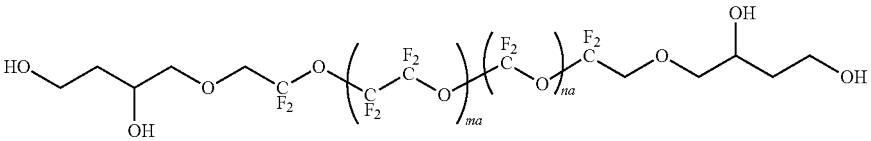

(3B)

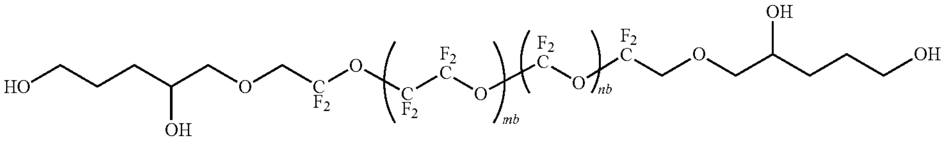

(3C)

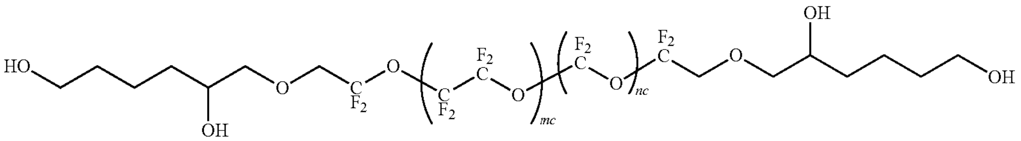

(3D)

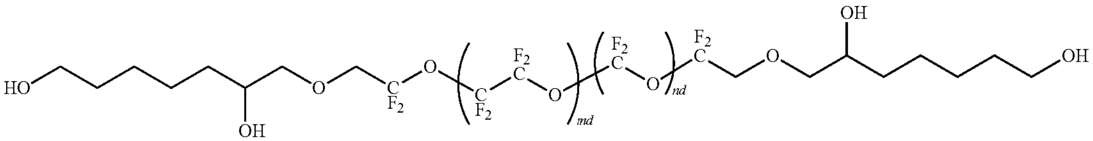

(3E)

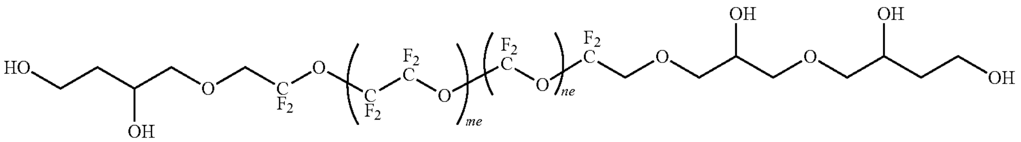

(3F)

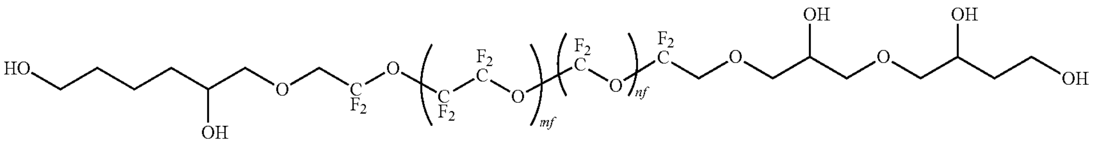

(3G)

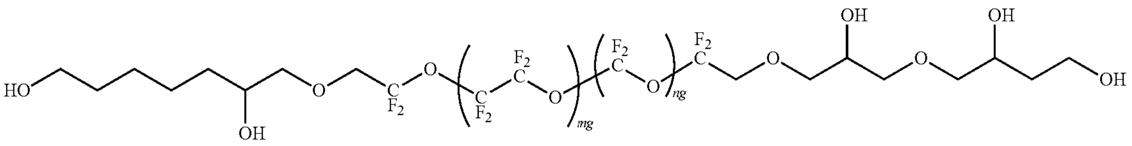

(yk in Formula (2K) indicates an average degree of polymerization and represents 0.1 to 30.)

(yl in Formula (2L) indicates an average degree of polymerization and represents 0.1 to 30.)

(ma and na in Formula (3A) indicate an average degree of polymerization and represent 0.1 to 30.)

(mb and nb in Formula (3B) indicate an average degree of polymerization and represent 0.1 to 30.)

(mc and nc in Formula (3C) indicate an average degree of polymerization and represent 0.1 to 30.)

(md and nd in Formula (3D) indicate an average degree of polymerization and represent 0.1 to 30.)

(me and ne in Formula (3E) indicate an average degree of polymerization and represent 0.1 to 30.)

(mf and nf in Formula (3F) indicate an average degree of polymerization and represent 0.1 to 30.)

(mg and ng in Formula (3G) indicate an average degree of polymerization and represent 0.1 to 30.)

(3H)

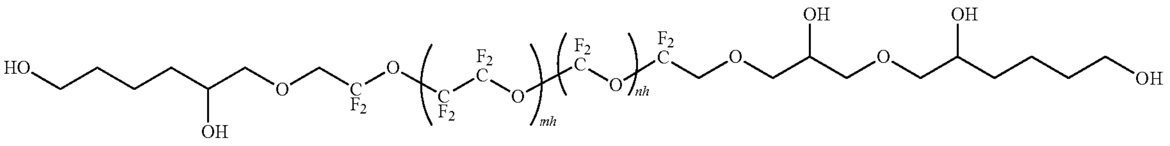

(3I)

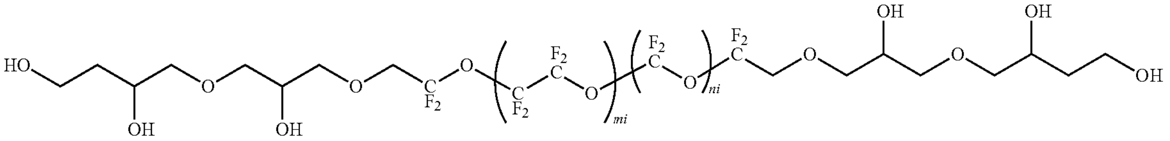

(3J)

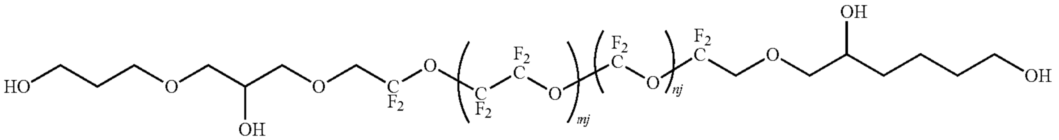

(3K)

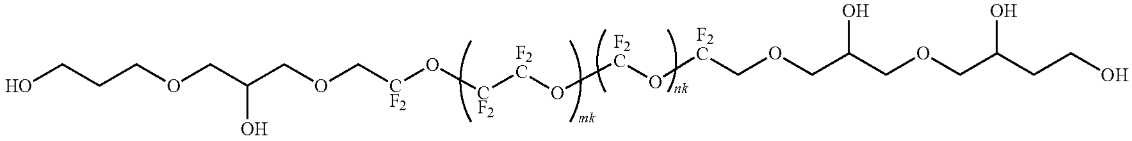

(3L)

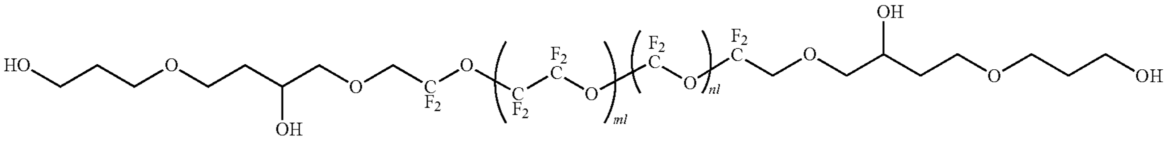

(3M)

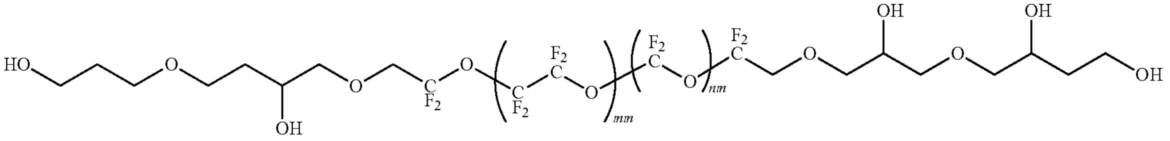

(3N)

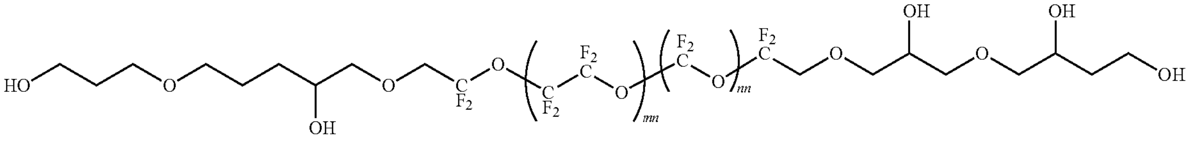

(3P)

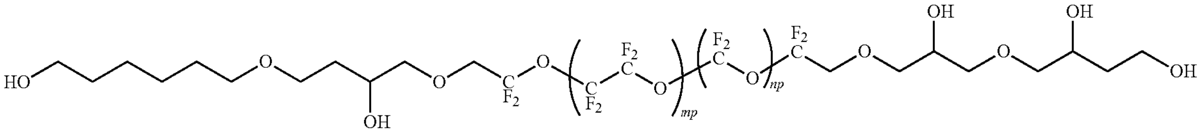

(mh and nh in Formula (3H) indicate an average degree of polymerization and represent 0.1 to 30.)

(mi and ni in Formula (3I) indicate an average degree of polymerization and represent 0.1 to 30.)

(mj and nj in Formula (3J) indicate an average degree of polymerization and represent 0.1 to 30.)

(mk and nk in Formula (3K) indicate an average degree of polymerization and represent 0.1 to 30.)

(ml and nl in Formula (3L) indicate an average degree of polymerization and represent 0.1 to 30.)

(mm and nm in Formula (3M) indicate an average degree of polymerization and represent 0.1 to 30.)

(mn and nn in Formula (3N) indicate an average degree of polymerization and represent 0.1 to 30.)

(mp and np in Formula (3P) indicate an average degree of polymerization and represent 0.1 to 30.)

If the compound represented by Formula (1) is any compound represented by Formulae (1A) to (1P), (2A) to (2P), and (3A) to (3P), the procurement of raw materials is easy and a lubricating layer capable of suppressing corrosion of a magnetic recording medium even if the lubricating layer has a thin thickness can be formed, which is preferable.

The fluorine-containing ether compound of the present embodiment can be arbitrarily selected, but preferably has a number average molecular weight (Mn) within a range of 500 to 10,000. If the number average molecular weight thereof is 500 or more, a lubricant containing the fluorine-containing ether compound of the present embodiment hardly evaporates, whereby the lubricant can be prevented from evaporating and transferring to a magnetic head. The number average molecular weight of the fluorine-containing ether compound is more preferably 1,000 or more. In addition, if the number average molecular weight thereof is 10,000 or less, the fluorine-containing ether compound has an appropriate viscosity, and a thin lubricating layer can be easily formed by applying a lubricant containing this fluorine-containing ether compound. The number average molecular weight of the fluorine-containing ether compound is preferably 3,000 or less because the viscosity of a lubricant becomes appropriate for handling in a case where the fluorine-containing ether compound is applied to the lubricant, which is more preferable. The number average molecular weight may be within a range of, for example, 500 to 3,000, 600 to 2,500, 700 to 2,000, 800 to 1,600, 900 to 1,500, 1,000 to 1,400, or 1,100 to 1,300.

The number average molecular weight (Mn) of the fluorine-containing ether compound is a value measured by $^{1}$H-NMR and $^{19}$F-NMR with AVANCE 111400 manufactured by Bruker BioSpin Group. In the nuclear magnetic resonance (NMR) measurement, a sample is diluted with a single or mixed solvent of hexafluorobenzene, acetone-d, tetrahydrofuran-d, and the like and used in the measurement. As the reference of the $^{19}$F-NMR chemical shift, the peak of hexafluorobenzene was set to −164.7 ppm, and as the reference of the $^{1}$H-NMR chemical shift, the peak of acetone was set to 2.2 ppm.

"Production Method"

A method for producing the fluorine-containing ether compound of the present embodiment is not particularly limited, and the fluorine-containing ether compound can be produced using a well-known conventional production method. The fluorine-containing ether compound of the present embodiment can be produced using, for example, a production method shown below.

First, a fluorine-based compound is prepared in which a hydroxymethyl group (—$CH_2OH$) is placed at both terminals of a perfluoropolyether chain corresponding to $R^3$ in Formula (1).

Next, the hydroxyl group of the hydroxymethyl group placed at one terminal of the fluorine-based compound is substituted with a group consisting of $R^1$—$R^2$—O— in Formula (1) (first reaction). Thereafter, the hydroxyl group of the hydroxymethyl group placed at the other terminal is substituted with a terminal group consisting of —O—$R^4$—$R^5$ in Formula (1) (second reaction).

The first reaction and the second reaction can be performed through a well-known conventional method, and can be appropriately determined according to the types of $R^1$, $R^2$, $R^4$, and $R^5$ in Formula (1). In addition, either of the first reaction and the second reaction may be performed first. In a case where $R^1$ is the same as $R^5$ and $R^2$ is the same as $R^4$, the first reaction and the second reaction may be performed at the same time.

The compound represented by Formula (1) is obtained through the above-described method.

In the present embodiment, it is preferable to use an epoxy compound to produce a fluorine-containing ether compound in which $R^2$ is represented by Formula (2) and $R^4$ is represented by Formula (3). As the epoxy compound, a commercially available product may be purchased and used. In addition, the epoxy compound may be synthesized by reacting alcohols having a structure corresponding to a terminal group represented by $R^1$ or $R^5$ of the fluorine-containing ether compound to be produced with any selected from epichlorohydrin, epibromohydrin, and 2-bromoethyloxirane. In addition, the epoxy compound may be synthesized through a method of oxidizing an unsaturated bond.

The fluorine-containing ether compound of the present embodiment is a compound represented by Formula (1) in which $R^2$ is represented by Formula (2), $R^4$ is represented by Formula (3), and $R^1$ and $R^5$ are a hydrogen atom or Formula (4). Furthermore, a and b in Formula (2) are an integer of 0 to 2, d and e in Formula (3) are an integer of 0 to 2, and at least one of b in Formula (2) and e in Formula (3) is 1 or more. Accordingly, the fluorine-containing ether compound shown in Formula (1) contains a total of 3 or more hydroxyl groups at $R^2$ and/or $R^4$ and both terminals of the chain structure. For this reason, a lubricating layer containing the fluorine-containing ether compound of the present embodiment has favorable adhesion properties with respect to a protective layer.

In addition, the fluorine-containing ether compound represented by Formula (1) has a perfluoropolyether chain (PFPE chain) represented by $R^3$. $R^3$ in the lubricating layer containing the fluorine-containing ether compound covers the surface of the protective layer and imparts water resistance to the lubricating layer due to its low surface energy. Moreover, in the fluorine-containing ether compound represented by Formula (1), c in Formula (2) is an integer of 2 to 5, f in Formula (3) is an integer of 2 to 5, and at least one of b in Formula (2) and e in Formula (3) is 1 or more. Accordingly, in the fluorine-containing ether compound represented by Formula (1), $R^2$ and/or $R^4$ have hydrophobic parts consisting of two or more linearly bound methylene groups. Therefore, the lubricating layer containing the fluorine-containing ether compound represented by Formula (1) has favorable water resistance and can prevent water from intruding into the magnetic recording medium because water hardly passes therethrough.

The fluorine-containing ether compound represented by Formula (1) has both hydrophobic parts (a PFPE chain and two or more linearly bound methylene groups) and hydrophilic parts (three or more hydroxyl groups) in the molecule. As a result, it is inferred that, in the lubricant containing the fluorine-containing ether compound represented by Formula (1), the hydrophilic parts in the fluorine-containing ether compound may interact with the protective layer and the hydrophobic parts may be arranged facing the surface on the side opposite to the protective layer. As a result, it is inferred that a lubricating layer can be obtained which has favorable adhesion properties with respect to the protective layer, can prevent water from intruding into the magnetic recording medium, and can suppress corrosion of the magnetic recording medium.

Furthermore, in a case where $R^1$ and/or $R^5$ in the fluorine-containing ether compound represented by Formula (1) is Formula (4), k in Formula (4) is an integer of 3 to 6. Therefore, the hydroxyl groups at one or both terminals of the chain structure are bound to three or more linearly bound methylene groups. Accordingly, it is inferred that the lubricating layer containing the fluorine-containing ether compound in which $R^1$ and/or $R^5$ are Formula (4) can prevent water from intruding into the magnetic recording medium and can more effectively suppress corrosion of the magnetic recording medium due to the hydrophobicity of the three or more linearly bound methylene groups.

[Lubricant for Magnetic Recording Medium]

A lubricant for a magnetic recording medium of the present embodiment contains the fluorine-containing ether compound represented by Formula (1).

The lubricant of the present embodiment can be used after being mixed as necessary with a well-known material that is used as a material for lubricants within the scope not impairing the characteristics imparted by containing the fluorine-containing ether compound represented by Formula (1).

Specific examples of well-known materials include FOMBLIN (registered trademark) ZDIAC, FOMBLIN ZDEAL, and FOMBLIN AM-2001 (all manufactured by Solvay Solexis), and Moresco A20H (manufactured by Moresco Corporation). The number average molecular weight of the well-known material that is used by being mixed with the lubricant of the present embodiment is preferably 1,000 to 10,000.

In a case where the lubricant of the present embodiment contains a material other than the fluorine-containing ether compound represented by Formula (1), the content of the fluorine-containing ether compound represented by Formula (1) in the lubricant of the present embodiment is preferably 50 mass % or more and more preferably 70 mass % or more. The content of the fluorine-containing ether compound represented by Formula (1) may be 80 mass % or more or 90 mass % or more. However, the present invention is not limited to these examples.

Since the lubricant of the present embodiment contains the fluorine-containing ether compound represented by Formula (1), the lubricating layer can be formed which has favorable adhesion properties with respect to the protective layer, can prevent water from intruding into the magnetic recording medium, and can suppress corrosion of the magnetic recording medium. The lubricating layer consisting of the lubricant of the present embodiment is highly effective in suppressing corrosion of a magnetic recording medium, and therefore can be made thin.

[Magnetic Recording Medium]

A magnetic recording medium of the present embodiment includes at least a magnetic layer, a protective layer, and a lubricating layer sequentially provided on a substrate.

In the magnetic recording medium of the present embodiment, one or more underlayers can be provided as necessary between the substrate and the magnetic layer.

In addition, it is also possible to provide an adhesive layer and/or a soft magnetic layer between the underlayer and the substrate.

The FIGURE is a schematic cross-sectional view showing one embodiment of a magnetic recording medium of the present invention.

A magnetic recording medium 10 of the present embodiment has a structure in which an adhesive layer 12, a soft magnetic layer 13, a first underlayer 14, a second underlayer 15, a magnetic layer 16, a protective layer 17, and a lubricating layer 18 are sequentially provided on a substrate 11.

"Substrate"

As the substrate 11, for example, a non-magnetic substrate or the like in which a NiP or NiP alloy film is formed on a base made of metal or alloy material such as Al or an Al alloy can be used.

In addition, as the substrate 11, a non-magnetic substrate made of a non-metal material such as glass, ceramics, silicon, silicon carbide, carbon or a resin may be used, and a non-magnetic substrate in which a NiP or NiP alloy film is formed on a base made of this non-metal material may also be used.

"Adhesive Layer"

The adhesive layer 12 prevents the progress of corrosion of the substrate 11 which may occur in a case where the substrate 11 and the soft magnetic layer 13, which is provided on the adhesive layer 12, are arranged in contact with each other.

The material of the adhesive layer 12 can be appropriately selected from, for example, Cr, a Cr alloy, Ti, a Ti alloy, CrTi, NiAl, and an AlRu alloy. The adhesive layer 12 can be formed by, for example, a sputtering method.

"Soft Magnetic Layer"

The soft magnetic layer 13 preferably has a structure in which a first soft magnetic film, an interlayer made of a Ru film, and a second soft magnetic film are sequentially laminated. That is, the soft magnetic layer 13 preferably has a structure in which the interlayer made of a Ru film is sandwiched between the two soft magnetic films, whereby the soft magnetic films on and under the interlayer are antiferromagnetically coupled (AFC).

Examples of the material of the first soft magnetic film and the second soft magnetic film include a CoZrTa alloy and a CoFe alloy.

Any of Zr, Ta and Nb is preferably added to the CoFe alloy that is used for the first soft magnetic film and the second soft magnetic film. This accelerates the amorphization of the first soft magnetic film and the second soft magnetic film, makes it possible to improve the orientation of the first underlayer (seed layer) and makes it possible to reduce the flying height of a magnetic head.

The soft magnetic layer 13 can be formed by, for example, a sputtering method.

"First Underlayer"

The first underlayer 14 is a layer for controlling the orientations and crystal sizes of the second underlayer 15 and the magnetic layer 16 that are provided on the first underlayer 14.

Examples of the first underlayer 14 include a Cr layer, a Ta layer, a Ru layer, a CrMo alloy layer, a CoW alloy layer, a CrW alloy layer, a CrV alloy layer, and a CrTi alloy layer.

The first underlayer 14 can be formed by, for example, a sputtering method.

"Second Underlayer"

The second underlayer 15 is a layer that controls the orientation of the magnetic layer 16 to be favorable. The second underlayer 15 is preferably a Ru or Ru alloy layer.

The second underlayer 15 may be a single layer or may be composed of a plurality of layers. In a case where the second underlayer 15 is composed of a plurality of layers, all of the layers may be composed of the same material or at least one layer may be composed of a different material.

The second underlayer 15 can be formed by, for example, a sputtering method.

"Magnetic Layer"

The magnetic layer 16 is made of a magnetic film in which the easy magnetization axis is directed in a perpendicular or parallel direction with respect to the substrate surface. The magnetic layer 16 is a layer containing Co and Pt and may be a layer further containing an oxide or Cr, B, Cu, Ta, Zr, or the like in order to improve SNR characteristics.

Examples of the oxide that is contained in the magnetic layer 16 include $SiO_2$, SiO, $Cr_2O_3$, CoO, $Ta_2O_3$, and $TiO_2$.

The magnetic layer 16 may be composed of a single layer or may be composed of a plurality of magnetic layers made of materials with different compositions.

For example, in a case where the magnetic layer 16 is composed of three layers of a first magnetic layer, a second magnetic layer, and a third magnetic layer sequentially laminated from below, the first magnetic layer is preferably a granular structure made of a material containing Co, Cr, and Pt and further containing an oxide. As the oxide that is contained in the first magnetic layer, for example, oxides of Cr, Si, Ta, Al, Ti, Mg, Co, or the like are preferably used. Among them, in particular, $TiO_2$, $Cr_2O_3$, $SiO_2$, and the like can be suitably used. In addition, the first magnetic layer is preferably made of a composite oxide to which two or more oxides have been added. Among them, in particular, $Cr_2O_3$—$SiO_2$, $Cr_2O_3$—$TiO_2$, $SiO_2$—$TiO_2$, and the like can be suitably used.

The first magnetic layer may contain, in addition to Co, Cr, Pt, and the oxide, one or more elements selected from B, Ta, Mo, Cu, Nd, W, Nb, Sm, Tb, Ru, and Re.

For the second magnetic layer, the same material as for the first magnetic layer can be used. The second magnetic layer preferably has a granular structure.

The third magnetic layer preferably has a non-granular structure made of a material containing Co, Cr, and Pt but containing no oxides. The third magnetic layer may contain, in addition to Co, Cr, and Pt, one or more elements selected from B, Ta, Mo, Cu, Nd, W, Nb, Sm, Tb, Ru, Re, and Mn.

In a case where the magnetic layer 16 is formed of a plurality of magnetic layers, a non-magnetic layer is preferably provided between the magnetic layers adjacent to each other. In a case where the magnetic layer 16 is made up of three layers of the first magnetic layer, the second magnetic layer and the third magnetic layer, it is preferable to provide a non-magnetic layer between the first magnetic layer and the second magnetic layer and a non-magnetic layer between the second magnetic layer and the third magnetic layer.

For the non-magnetic layer that is provided between the magnetic layers adjacent to each other in the magnetic layer 16, it is possible to suitably use, for example, Ru, a Ru alloy, a CoCr alloy, and a CoCrX1 alloy (X1 represents one or more elements selected from Pt, Ta, Zr, Re, Ru, Cu, Nb, Ni, Mn, Ge, Si, O, N, W, Mo, Ti, V, and B).

For the non-magnetic layer that is provided between the magnetic layers adjacent to each other in the magnetic layer 16, an alloy material containing an oxide, a metallic nitride or a metallic carbide is preferably used. Specifically, as the oxide, for example, $SiO_2$, $Al_2O_3$, $Ta_2O_5$, $Cr_2O_3$, MgO, $Y_2O_3$, and $TiO_2$ can be used. As the metallic nitride, for example, AlN, $Si_3N_4$, TaN, and CrN can be used. As the metallic carbide, for example, TaC, BC, and SiC can be used.

The non-magnetic layer can be formed by, for example, a sputtering method.

The magnetic layer 16 is preferably a magnetic layer for perpendicular magnetic recording in which the easy magnetization axis is directed in a direction perpendicular to the substrate surface in order to realize a higher recording density. The magnetic layer 16 may be a magnetic layer for in-plane magnetic recording.

The magnetic layer 16 may be formed by any well-known conventional method such as a deposition method, an ion beam sputtering method, or a magnetron sputtering method. The magnetic layer 16 is normally formed by a sputtering method.

"Protective layer" The protective layer 17 protects the magnetic layer 16. The protective layer 17 may be composed of a single layer or may be composed of a plurality of layers. As the material of the protective layer 17, carbon, nitrogen-containing carbon, silicon carbide, and the like can be exemplified.

As the protective layer 17, a carbon-based protective layer can be preferably used, and, in particular, an amorphous carbon protective layer is preferable. When the protective layer 17 is a carbon-based protective layer, an interaction with the hydroxyl group contained in the fluorine-containing ether compound in the lubricating layer 18 is further enhanced, which is preferable.

The adhesive force between the carbon-based protective layer and the lubricating layer 18 can be controlled by forming the carbon-based protective layer with hydrogenated carbon and/or nitrogenated carbon and adjusting the hydrogen content and/or the nitrogen content in the carbon-based protective layer. The hydrogen content in the carbon-based protective layer is preferably 3 to 20 atomic % when measured by the hydrogen forward scattering method (HFS). In addition, the nitrogen content in the carbon-based protective layer is preferably 4 to 15 atomic % when measured by X-ray photoelectron spectroscopy (XPS).

The hydrogen and/or nitrogen that are contained in the carbon-based protective layer do not need to be uniformly contained throughout the entire carbon-based protective layer. The carbon-based protective layer is suitably formed as a composition gradient layer in which nitrogen is contained in the lubricating layer 18 side of the protective layer 17 and hydrogen is contained in the magnetic layer 16 side of the protective layer 17. In this case, the adhesive force between the magnetic layer 16 and the carbon-based protective layer and the adhesive force between the lubricating layer 18 and the carbon-based protective layer further improve.

The film thickness of the protective layer 17 may be set to 1 nm to 7 nm. When the film thickness of the protective layer 17 is 1 nm or more, performance as the protective layer 17 can be sufficiently obtained. The film thickness of the protective layer 17 is preferably 7 nm or less from the viewpoint of reducing the thickness of the protective layer 17.

As a method for forming the protective layer 17, it is possible to use a sputtering method in which a carbon-containing target material is used, a chemical vapor deposition (CVD) method in which a hydrocarbon raw material such as ethylene or toluene is used, an ion beam deposition (IBD) method, and the like.

In the case of forming a carbon-based protective layer as the protective layer 17, the carbon-based protective layer can be formed by, for example, a DC magnetron sputtering method. Particularly, in the case of forming a carbon-based protective layer as the protective layer 17, an amorphous carbon protective layer is preferably formed by a plasma CVD method. The amorphous carbon protective layer formed by the plasma CVD method has a uniform surface with small roughness.

"Lubricating Layer"

The lubricating layer 18 prevents contamination of the magnetic recording medium 10. In addition, the lubricating layer 18 reduces frictional force of a magnetic head of a magnetic recording/reproducing device, which slides on the magnetic recording medium 10, thereby improving the durability of the magnetic recording medium 10.

The lubricating layer 18 is formed in contact with the protective layer 17 as shown in the FIGURE. The lubricating layer 18 contains the above-described fluorine-containing ether compound.

In a case where the protective layer 17, which is placed below the lubricating layer 18, is a carbon-based protective layer, particularly, the lubricating layer 18 is bound to the protective layer 17 with a high binding force. As a result, the magnetic recording medium 10 in which the surface of the protective layer 17 is coated with the lubricating layer 18 at a high coating rate in spite of a thin thickness is likely to be obtained, and contamination on the surface of the magnetic recording medium 10 can be effectively prevented.

The average film thickness of the lubricating layer 18 is preferably 0.5 nm (5 Å) to 2.0 nm (20 Å) and more preferably 0.5 nm (5 Å) to 1.0 nm (10 Å). When the average film thickness of the lubricating layer 18 is 0.5 nm or more, the lubricating layer 18 does not have an island shape or a mesh shape and is formed in a uniform film thickness. For this reason, the surface of the protective layer 17 can be coated with the lubricating layer 18 at a high coating rate. In addition, when the average film thickness of the lubricating layer 18 is set to 2.0 nm or less, it is possible to sufficiently reduce the thickness of the lubricating layer 18 and to sufficiently decrease the flying height of a magnetic head.

In a case where the surface of the protective layer 17 is not sufficiently coated with the lubricating layer 18 at a high coating rate, an environmental substance adsorbed to the surface of the magnetic recording medium 10 passes through voids in the lubricating layer 18 and intrudes into the layer below the lubricating layer 18. The environmental substance that has intruded into the layer below the lubricating layer 18 is adsorbed and bound to the protective layer 17 and generates a contamination substance. At the time of reproducing magnetic records, the generated contamination substance (aggregated component) adheres (transfers) to a magnetic head as a smear to break the magnetic head or degrade the magnetic recording/reproducing characteristics of magnetic recording/reproducing devices.

Examples of the environmental substance that generates the contamination substance include siloxane compounds (cyclic siloxane and linear siloxane), ionic impurities, hydrocarbons having a relatively high molecular weight such as octacosane, and plasticizers such as dioctyl phthalate. Examples of metal ions contained in the ionic impurities include a sodium ion and a potassium ion. Examples of inorganic ions contained in the ionic impurities include a chlorine ion, a bromine ion, a nitrate ion, a sulfate ion, and an ammonium ion. Examples of organic ions contained in the ionic impurities include an oxalate ion and a formate ion.

"Method for Forming Lubricating Layer"

Examples of methods for forming the lubricating layer 18 include a method in which a magnetic recording medium that is not yet fully manufactured and thus includes the individual layers up to the protective layer 17 formed on the substrate 11 is prepared and a solution for forming a lubricating layer is applied onto the protective layer 17 and dried.

The solution for forming a lubricating layer can be obtained by dispersing and dissolving the above-described lubricant for a magnetic recording medium of the embodiment in a solvent as necessary and adjusting the viscosity and concentration to be suitable for application methods.

Examples of solvents used for the solution for forming a lubricating layer include fluorine-based solvents such as VERTREL (registered trademark) XF (trade name, manufactured by Dupont-Mitsui Fluorochemicals Co., Ltd.).

A method for applying the solution for forming a lubricating layer is not particularly limited, and examples thereof include a spin coating method, a spraying method, a paper coating method, and a dipping method.

In a case of using a dipping method, it is possible to use, for example, a method shown below. First, the substrate 11 on which the individual layers up to the protective layer 17 have been formed is immersed in the solution for forming a lubricating layer that has been placed in an immersion vessel of a dip coater. Next, the substrate 11 is lifted from the immersion vessel at a predetermined speed. As a result, the solution for forming a lubricating layer is applied to the surface of the protective layer 17 on the substrate 11.

The use of the dipping method makes it possible to uniformly apply the solution for forming a lubricating layer to the surface of the protective layer 17 and makes it possible to form the lubricating layer 18 on the protective layer 17 in a uniform film thickness.

In the present embodiment, a burnishing (precision polishing) step is preferably performed after the lubricating layer 18 is formed on the surface of the substrate 11. By performing the burnishing step, projection defects and particles present on the surface of the substrate 11 on which the lubricating layer 18 has been formed can be removed, and the magnetic recording medium 10 with a smooth surface can be obtained. If the surface of the magnetic recording medium 10 is smooth, the spacing loss with a magnetic head can be reduced and the signal characteristics may improve, which is preferable.

As the burnishing step, for example, a step of scanning burnishing tape on the surface of the substrate 11 on which the lubricating layer 18 has been formed can be performed. As the burnishing tape, one made of a resin film holding abrasive grains can be used. The grain size of the abrasive grains can be set to, for example, #6000 to #20000.

In the present embodiment, a heat treatment is preferably carried out on the substrate 11 on which the lubricating layer 18 has been formed. The heat treatment improves the adhesion properties between the lubricating layer 18 and the protective layer 17 and improves the adhesive force between the lubricating layer 18 and the protective layer 17.

The heat treatment temperature is preferably set to 100° C. to 180° C. When the heat treatment temperature is 100° C. or higher, an effect on improvement in the adhesion properties between the lubricating layer 18 and the protective layer 17 can be sufficiently obtained. In addition, when the heat treatment temperature is set to 180° C. or lower, it is possible to prevent thermal decomposition of the lubricating layer 18. The heat treatment time is preferably set to 10 to 120 minutes.

The magnetic recording medium 10 of the present embodiment includes at least the magnetic layer 16, the protective layer 17, and the lubricating layer 18 sequentially provided on the substrate 11. In the magnetic recording medium 10 of the present embodiment, the lubricating layer 18 containing the above-described fluorine-containing ether compound is formed in contact with the protective layer 17. This lubricating layer 18 is highly effective in suppressing corrosion of the magnetic recording medium 10. For this reason, the magnetic recording medium 10 of the present embodiment has less contamination substances present on the surface, has excellent corrosion resistance, and has favorable reliability and durability. In addition, since the magnetic recording medium 10 of the present embodiment has the lubricating layer 18 highly effective in suppressing corrosion, the thickness of the protective layer 17 and/or the lubricating layer 18 can be reduced. In addition, in the lubricating layer 18 in the magnetic recording medium 10 of the present embodiment, foreign matters (smears) are less likely to be generated, and pickup can be suppressed.

EXAMPLES

Hereinafter, the present invention will be described more specifically with reference to examples and comparative examples. The present invention is not limited to the following examples.

Example 1

10.3 g of a compound represented by $HOCH_2CF_2CF_2O(CF_2CF_2CF_2O)_zCF_2CF_2CH_2OH$ (z in the formula was 4.5) (number average molecular weight: 1,025, molecular weight distribution: 1.1), 3.44 g of a compound represented by Formula (12) below, and 10 mL of t-butanol were added to a 100 mil eggplant flask under a nitrogen gas atmosphere and stirred until the mixture became uniform at room temperature. 0.34 g of potassium tert-butoxide was further added to this uniform solution and reacted by being stirred at 70° C. for 30 hours to obtain a reaction product.

The compound represented by Formula (12) was obtained by protecting the hydroxyl group of 3-buten-1-ol with a tetrahydropyranyl (THP) group and then oxidizing the double bond.

(12)

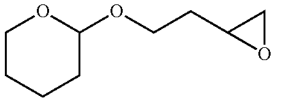

The obtained reaction product was allowed to cool to 25° C., and 20 g of 10% hydrogen chloride/methanol solution (a hydrogen chloride-methanol reagent (5% to 10%) manufactured by Tokyo Chemical Industry Co., Ltd.) was added thereto and stirred at room temperature for 2 hours. The reaction solution was moved little by little to a separatory funnel containing 70 mL of 8% sodium bicarbonate water and extracted twice with 150 mL of ethyl acetate. An organic layer was washed with water and dehydrated with anhydrous sodium sulfate (drying agent).

After filtering the drying agent, the filtrate was concentrated, and the residue was purified through silica gel column chromatography to obtain 7.65 g of a compound (1A) (in Formula (1A), za indicating the average degree of polymerization was 4.5).

$^1$H-NMR measurement of the obtained compound (1A) was carried out, and the structure was identified from the following results.

Compound (1A); $^1$H-NMR ($CD_3COCD_3$);

δ [ppm] 1.3-1.7 (4H), 3.4-4.2 (18H)

Example 2

The same operation as in Example 1 was carried out except that 3.73 g of the compound represented by Formula (13) below was used instead of the compound represented by Formula (12), thereby obtaining 7.83 g of a compound (1B) (in Formula (1B), zb indicating the average degree of polymerization was 4.5).

The compound (13) was obtained by protecting the hydroxyl group of 4-penten-1-ol with a THP group and then oxidizing the double bond.

(13)

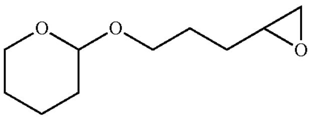

$^1$H-NMR measurement of the obtained compound (1B) was carried out, and the structure was identified from the following results.

Compound (1B); $^1$H-NMR ($CD_3COCD_3$);

δ [ppm] 1.3-1.7 (8H), 3.4-4.2 (18H)

Example 3

The same operation as in Example 1 was carried out except that 3.73 g of the compound represented by Formula (14) below was used instead of the compound represented by Formula (12), thereby obtaining 8.01 g of a compound (1C) (in Formula (1C), zc indicating the average degree of polymerization was 4.5).

The compound (14) was obtained by protecting the hydroxyl group of 5-hexen-1-ol with a THP group and then oxidizing the double bond.

(14)

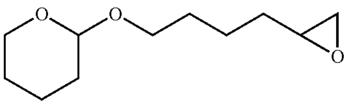

$^1$H-NMR measurement of the obtained compound (1C) was carried out, and the structure was identified from the following results.

Compound (1C); $^1$H-NMR ($CD_3COCD_3$);

δ [ppm] 1.3-1.7 (12H), 3.4-4.2 (18H)

Example 4

The same operation as in Example 1 was carried out except that 3.73 g of the compound represented by Formula (15) below was used instead of the compound represented by Formula (12), thereby obtaining 8.19 g of a compound (1D) (in Formula (1D), zd indicating the average degree of polymerization was 4.5).

The compound (15) was obtained by protecting the hydroxyl group of 6-hepten-1-ol with a THP group and then oxidizing the double bond.

(15)

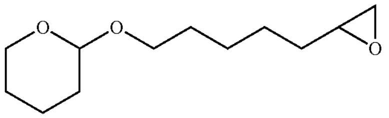

$^1$H-NMR measurement of the obtained compound (1D) was carried out, and the structure was identified from the following results.

Compound (1D); $^1$H-NMR ($CD_3COCD_3$);

δ [ppm] 1.3-1.7 (16H), 3.4-4.2 (18H)

Example 5

20.0 g of the compound represented by $HOCH_2CF_2CF_2O(CF_2CF_2CF_2O)_zCF_2CF_2CH_2OH$ (z in the formula was 4.5) (number average molecular weight: 1,025, molecular weight distribution: 1.1), 2.07 g of a compound represented by Formula (12) above, and 20 mL of t-butanol were added to a 100 ml eggplant flask under a nitrogen gas atmosphere and stirred until the mixture became uniform at room temperature. 0.67 g of potassium tert-butoxide was further added to this uniform solution and reacted by being stirred at 70° C. for 30 hours to obtain a reaction product.

The obtained reaction product was cooled to 25° C., moved to a separatory funnel containing 50 mL of water, and extracted twice with 150 mL of ethyl acetate. An organic layer was washed with water and dehydrated with anhydrous sodium sulfate (drying agent).

After filtering the drying agent, the filtrate was concentrated, and the residue was purified through silica gel column chromatography to obtain 9.38 g of a compound represented by Formula (16).

(16)

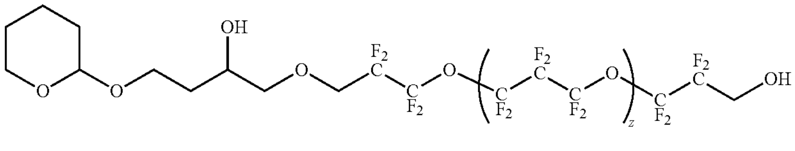

(In Formula (16), z indicating the average degree of polymerization was 4.5.)

9.30 g of the compound represented by Formula (16) above, 1.99 g of a compound represented by Formula (17) below, and 25 mL of t-butanol were added to a 100 mL eggplant flask in a nitrogen gas atmosphere and stirred until the mixture became uniform at room temperature. 0.14 g of potassium tert-butoxide was added to this uniform solution and reacted by being stirred at 70° C. for 16 hours.

The compound represented by Formula (17) was obtained by reacting 1,2,4-butanetriol with benzaldehyde to obtain an acetal compound and then reacting it with epibromohydrin.

(17)

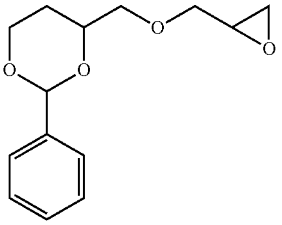

The obtained reaction product was allowed to cool to 25° C., and 20 g of 10% hydrogen chloride/methanol solution (a hydrogen chloride-methanol reagent (5% to 10%) manufactured by Tokyo Chemical Industry Co., Ltd.) was added thereto and stirred at room temperature for 2 hours. The reaction solution was moved little by little to a separatory funnel containing 70 mL of 8% sodium bicarbonate water and extracted twice with 150 mL of ethyl acetate. An organic layer was washed with water and dehydrated with anhydrous sodium sulfate (drying agent).

After filtering the drying agent, the filtrate was concentrated, and the residue was purified through silica gel column chromatography to obtain 6.45 g of a compound (1E) (in Formula (1E), ze indicating the average degree of polymerization was 4.5).

$^1$H-NMR measurement of the obtained compound (1E) was carried out, and the structure was identified from the following results.

Compound (1E); $^1$H-NMR ($CD_3COCD_3$);

δ [ppm] 1.5-1.8 (4H), 3.4-4.2 (24H)

Example 6

The same operation as in Example 5 was carried out except that 9.60 g of a compound represented by Formula (18) below was obtained as an intermediate using 2.40 g of the compound represented by Formula (14) above instead of the compound represented by Formula (12), thereby obtaining 6.58 g of Formula (1F) (in Formula (1F), zf indicating the average degree of polymerization was 4.5).

(18)

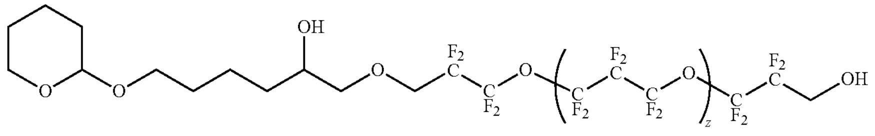

(In Formula (18), z indicating the average degree of polymerization was 4.5.)

$^{1}$H-NMR measurement of the obtained compound (1F) was carried out, and the structure was identified from the following results.

Compound (1F); $^{1}$H-NMR ($CD_3COCD_3$);

δ [ppm] 1.3-1.7 (8H), 3.4-4.2 (24H)

Example 7

The same operation as in Example 5 was carried out except that 9.70 g of a compound represented by Formula (19) below was obtained as an intermediate using 2.57 g of the compound represented by Formula (15) above instead of the compound represented by Formula (12), thereby obtaining 6.50 g of Formula (1G) (in Formula (1G), zg indicating the average degree of polymerization was 4.5).

(20)

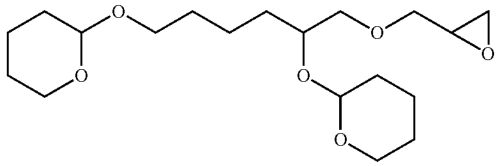

$^{1}$H-NMR measurement of the obtained compound (1H) was carried out, and the structure was identified from the following results.

Compound (1H); $^{1}$H-NMR ($CD_3COCD_3$);

δ [ppm] 1.3-1.7 (14H), 3.4-4.2 (24H)

(19)

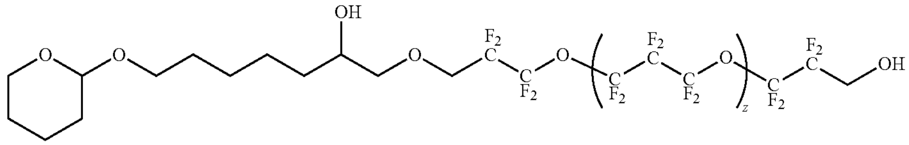

(In Formula (19), z indicating the average degree of polymerization was 4.5.)

$^{1}$H-NMR measurement of the obtained compound (1G) was carried out, and the structure was identified from the following results.

Compound (1G); $^{1}$H-NMR ($CD_3COCD_3$);

δ [ppm] 1.3-1.7 (10H), 3.4-4.2 (24H)

Example 8

The compound represented by Formula (18) was synthesized as an intermediate using 2.40 g of the compound represented by Formula (14) above instead of the compound represented by Formula (12). Then, the same operation as in Example 5 was carried out except that 2.84 g of a compound represented by Formula (20) below was used instead of the compound represented by Formula (17), thereby obtaining 6.69 g of Formula (1H) (in Formula (1H), zh indicating the average degree of polymerization was 4.5).

The compound represented by Formula (20) was obtained by protecting the hydroxyl group of a compound obtained by reacting the compound represented by Formula (14) with allyl alcohol with a THP group, and oxidizing the double bond.

Example 9

The same operation as in Example 1 was carried out except that 5.00 g of the compound represented by Formula (17) was used instead of the compound represented by Formula (12), thereby obtaining 8.55 g of a compound (1I) (in Formula (1I), zi indicating the average degree of polymerization was 4.5).

$^{1}$H-NMR measurement of the obtained compound (1I) was carried out, and the structure was identified from the following results.

Compound (1I); $^{1}$H-NMR ($CD_3COCD_3$);

δ [ppm] 1.3-1.7 (4H), 3.4-4.2 (30H)

Example 10

The compound represented by Formula (18) was synthesized as an intermediate using 2.40 g of the compound represented by Formula (14) instead of the compound represented by Formula (12). Then, the same operation as in Example 5 was carried out except that 1.68 g of a compound represented by Formula (21) below was used instead of the compound represented by Formula (17), thereby obtaining 6.26 g of Formula (1J) (in Formula (1J), zj indicating the average degree of polymerization was 4.5).

The compound represented by Formula (21) was obtained by protecting one hydroxyl group of propanediol with a THP group and reacting epibromohydrin with the other hydroxyl group.

(21)

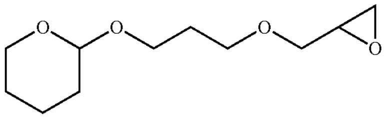

$^{1}H$-NMR measurement of the obtained compound (1J) was carried out, and the structure was identified from the following results.

Compound (1J); $^{1}H$-NMR ($CD_3COCD_3$);

δ [ppm] 1.5-1.8 (8H), 3.4-4.2 (22H)

Example 11

The same operation as in Example 5 was carried out except that 9.73 g of a compound represented by Formula (22) below was obtained as an intermediate using 2.60 g of the compound represented by Formula (21) above instead of the compound represented by Formula (12), thereby obtaining 6.26 g of Formula (1K) (in Formula (1K), zk indicating the average degree of polymerization was 4.5).

(22)

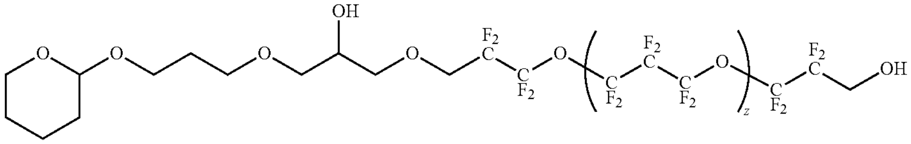

(In Formula (22), z indicating the average degree of polymerization was 4.5.)

$^{1}H$-NMR measurement of the obtained compound (1K) was carried out, and the structure was identified from the following results.

Compound (1K); $^{1}H$-NMR ($CD_3COCD_3$);

δ [ppm] 1.5-1.8 (4H), 3.4-4.2 (28H)

Example 12

The same operation as in Example 1 was carried out except that 4.61 g of a compound represented by Formula (23) below was used instead of the compound represented by Formula (12), thereby obtaining 8.40 g of a compound (1L) (in Formula (1L), zl indicating the average degree of polymerization was 4.5).

The compound represented by Formula (23) was obtained by oxidizing the double bond of a compound obtained by reacting 3-buten-1-ol with 2-(3-chloropropoxy)tetrahydro-2H-pyran.

(23)

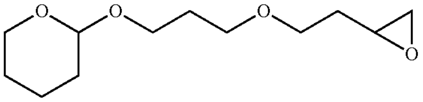

$^{1}H$-NMR measurement of the obtained compound (1L) was carried out, and the structure was identified from the following results.

Compound (1L); $^{1}H$-NMR ($CD_3COCD_3$);

δ [ppm] 1.3-1.7 (8H), 3.4-4.2 (26H)

Example 13

The same operation as in Example 5 was carried out except that 9.82 g of a compound represented by Formula (24) below was obtained as an intermediate using 2.76 g of the compound represented by Formula (23) above instead of the compound represented by Formula (12), thereby obtaining 6.71 g of Formula (1M) (in Formula (1M), zm indicating the average degree of polymerization was 4.5).

(24)

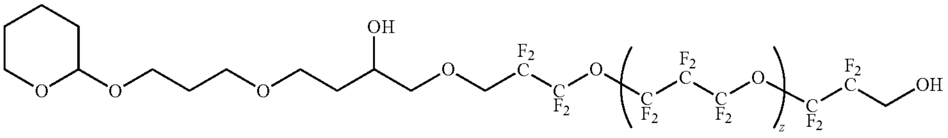

(In Formula (24), z indicating the average degree of polymerization was 4.5.)

$^1$H-NMR measurement of the obtained compound (1M) was carried out, and the structure was identified from the following results.

Compound (1M); $^1$H-NMR ($CD_3COCD_3$);

δ [ppm] 1.5-1.8 (6H), 3.4-4.2 (28H)

Example 14

The same operation as in Example 5 was carried out except that 9.99 g of a compound represented by Formula (26) below was obtained as an intermediate using 2.93 g of a compound represented by Formula (25) below instead of the compound represented by Formula (12), thereby obtaining 6.62 g of Formula (1N) (in Formula (1N), zn indicating the average degree of polymerization was 4.5).

The compound represented by Formula (25) was obtained by oxidizing the double bond of a compound obtained by reacting 4-penten-1-ol with 2-(3-chloropropoxy)tetrahydro-2H-pyran.

(25)

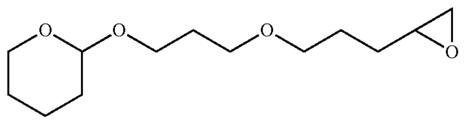

(26)

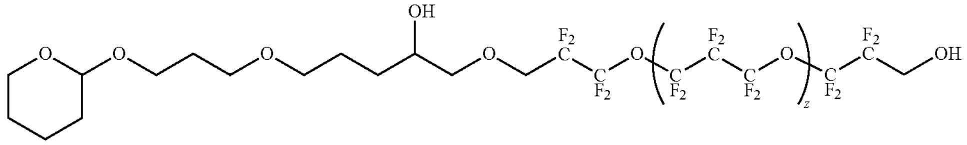

(In Formula (26), z indicating the average degree of polymerization was 4.5.)

$^1$H-NMR measurement of the obtained compound (1N) was carried out, and the structure was identified from the following results.

Compound (1N); $^1$H-NMR ($CD_3COCD_3$);

δ [ppm] 1.5-1.8 (8H), 3.4-4.2 (28H)

Example 15

The same operation as in Example 5 was carried out except that 10.10 g of a compound represented by Formula (28) below was obtained as an intermediate using 3.27 g of a compound represented by Formula (27) below instead of the compound represented by Formula (12), thereby obtaining 6.80 g of Formula (1P) (in Formula (1P), zp indicating the average degree of polymerization was 4.5).

The compound represented by Formula (27) was obtained by protecting one hydroxyl group of hexanediol with a THP group and reacting 2-bromoethyloxirane with the other hydroxyl group.

(27)

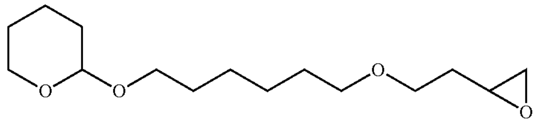

(28)

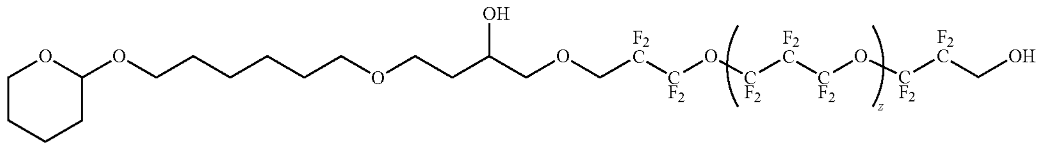

(In Formula (28), z indicating the average degree of polymerization was 4.5.)

$^1$H-NMR measurement of the obtained compound (1P) was carried out, and the structure was identified from the following results.

Compound (1P); $^1$H-NMR ($CD_3COCD_3$);

δ [ppm] 1.5-1.8 (12H), 3.4-4.2 (28H)

Examples 16 to 30

The same operations as in Examples 1 to 15 were carried out except that the compound represented by $HOCH_2CF_2O(CF_2CF_2O)_mCF_2CH_2OH$ (m in the formula was 7.0) (number average molecular weight: 1,000, molecular weight distribution: 1.1) was used instead of the compound represented by $HOCH_2CF_2CF_2O(CF_2CF_2CF_2O)_zCF_2CF_2CH_2OH$ (z in the formula was 4.5) (number average molecular weight: 1,025, molecular weight distribution: 1.1), thereby obtaining Formulae (2A) to (2P).

$^1$H-NMR measurement of the obtained compound (2A) (In Formula (2A), ya indicating the average degree of polymerization was 7.0) was carried out, and the structure was identified from the following results.

Compound (2A); $^1$H-NMR ($CD_3COCD_3$);

δ [ppm] 1.3-1.7 (4H), 3.4-4.2 (18H)

$^1$H-NMR measurement of the obtained compound (2B) (In Formula (2B), yb indicating the average degree of polymerization was 7.0) was carried out, and the structure was identified from the following results.

Compound (2B); $^1$H-NMR ($CD_3COCD_3$);

δ [ppm] 1.3-1.7 (811), 3.4-4.2 (18H) $^1$H-NMR measurement of the obtained compound (2C) (In Formula (2C), yc indicating the average degree of polymerization was 7.0) was carried out, and the structure was identified from the following results.

Compound (2C); $^1$H-NMR ($CD_3COCD_3$);

δ [ppm] 1.3-1.7 (12H), 3.4-4.2 (18H)

$^1$H-NMR measurement of the obtained compound (2D) (In Formula (2D), yd indicating the average degree of polymerization was 7.0) was carried out, and the structure was identified from the following results.

Compound (2D); $^1$H-NMR ($CD_3COCD_3$);

δ [ppm] 1.3-1.7 (16H), 3.4-4.2 (18H)

$^1$H-NMR measurement of the obtained compound (2E) (In Formula (2E), ye indicating the average degree of polymerization was 7.0) was carried out, and the structure was identified from the following results.

Compound (2E); $^1$H-NMR ($CD_3COCD_3$);

δ [ppm] 1.5-1.8 (411), 3.4-4.2 (24H)

$^1$H-NMR measurement of the obtained compound (2F) (In Formula (2F), yf indicating the average degree of polymerization was 7.0) was carried out, and the structure was identified from the following results.

Compound (2F); $^1$H-NMR ($CD_3COCD_3$);

δ [ppm] 1.3-1.7 (8H), 3.4-4.2 (24H)

$^1$H-NMR measurement of the obtained compound (2G) (In Formula (2G), yg indicating the average degree of polymerization was 7.0) was carried out, and the structure was identified from the following results.

Compound (2G); $^1$H-NMR ($CD_3COCD_3$);

δ [ppm] 1.3-1.7 (10H), 3.4-4.2 (24H)

$^1$H-NMR measurement of the obtained compound (211) (In Formula (211), yh indicating the average degree of polymerization was 7.0) was carried out, and the structure was identified from the following results.

Compound (2H); $^1$H-NMR ($CD_3COCD_3$);

δ [ppm] 1.3-1.7 (14H), 3.4-4.2 (24H)

$^1$H-NMR measurement of the obtained compound (2I) (In Formula (2I), yi indicating the average degree of polymerization was 7.0) was carried out, and the structure was identified from the following results.

Compound (2I); 1H-NMR ($CD_3COCD_3$);

δ [ppm] 1.3-1.7 (4H), 3.4-4.2 (30H)

$^1$H-NMR measurement of the obtained compound (2J) (In Formula (2J), yj indicating the average degree of polymerization was 7.0) was carried out, and the structure was identified from the following results.

Compound (2J); $^1$H-NMR ($CD_3COCD_3$);

δ [ppm] 1.5-1.8 (811), 3.4-4.2 (22H)

$^1$H-NMR measurement of the obtained compound (2K) (In Formula (2K), yk indicating the average degree of polymerization was 7.0) was carried out, and the structure was identified from the following results.

Compound (2K); $^1$H-NMR ($CD_3COCD_3$);

δ [ppm] 1.5-1.8 (4H), 3.4-4.2 (28H)

$^1$H-NMR measurement of the obtained compound (2L) (In Formula (2L), yl indicating the average degree of polymerization was 7.0) was carried out, and the structure was identified from the following results.

Compound (2L); $^1$H-NMR ($CD_3COCD_3$);

δ [ppm] 1.3-1.7 (8H), 3.4-4.2 (26H)

$^1$H-NMR measurement of the obtained compound (2M) (In Formula (2M), ym indicating the average degree of polymerization was 7.0) was carried out, and the structure was identified from the following results.

Compound (2M); $^1$H-NMR ($CD_3COCD_3$);

δ [ppm] 1.5-1.8 (611), 3.4-4.2 (28H)

$^1$H-NMR measurement of the obtained compound (2N) (In Formula (2N), yn indicating the average degree of polymerization was 7.0) was carried out, and the structure was identified from the following results.

Compound (2N); $^1$H-NMR ($CD_3COCD_3$);

δ [ppm] 1.5-1.8 (811), 3.4-4.2 (28H)

$^1$H-NMR measurement of the obtained compound (2P) (In Formula (2P), yp indicating the average degree of polymerization was 7.0) was carried out, and the structure was identified from the following results.

Compound (2P); $^1$H-NMR ($CD_3COCD_3$);

δ [ppm] 1.5-1.8 (12H), 3.4-4.2 (28H)

Examples 31 to 45

The same operations as in Examples 1 to 15 were carried out except that a compound represented by $HOCH_2CF_2O(CF_2CF_2O)_m(CF_2O)_nCF_2CH_2OH$ (in the formula, m was 4.5 and n was 4.5) (number average molecular weight: 1,000, molecular weight distribution: 1.1) was used instead of the compound represented by $HOCH_2CF_2CF_2O(CF_2CF_2CF_2O)_zCF_2CF_2CH_2OH$ (z in the formula was 4.5) (number average molecular weight: 1,025, molecular weight distribution: 1.1), thereby obtaining Formulae (3A) to (3P).

$^1$H-NMR measurement of the obtained compound (3A) (In Formula (3A), ma and na indicating the average degree of polymerization was 4.5) was carried out, and the structure was identified from the following results.

Compound (3A); $^1$H-NMR ($CD_3COCD_3$);

δ [ppm] 1.3-1.7 (4H), 3.4-4.2 (18H)

$^1$H-NMR measurement of the obtained compound (3B) (In Formula (3B), mb and nb indicating the average degree of polymerization was 4.5) was carried out, and the structure was identified from the following results.

Compound (3B); $^1$H-NMR ($CD_3COCD_3$);

δ [ppm] 1.3-1.7 (811), 3.4-4.2 (18H)

$^1$H-NMR measurement of the obtained compound (3C) (In Formula (3C), mc and nc indicating the average degree of polymerization was 4.5) was carried out, and the structure was identified from the following results.

Compound (3C); $^1$H-NMR ($CD_3COCD_3$);

δ [ppm] 1.3-1.7 (12H), 3.4-4.2 (18H)

$^1$H-NMR measurement of the obtained compound (3D) (In Formula (3D), md and nd indicating the average degree of polymerization was 4.5) was carried out, and the structure was identified from the following results.

Compound (3D); $^1$H-NMR ($CD_3COCD_3$);

δ [ppm] 1.3-1.7 (16H), 3.4-4.2 (18H)

$^1$H-NMR measurement of the obtained compound (3E) (In Formula (3E), me and ne indicating the average degree of polymerization was 4.5) was carried out, and the structure was identified from the following results.

Compound (3E); $^1$H-NMR ($CD_3COCD_3$);

δ [ppm] 1.5-1.8 (4H), 3.4-4.2 (24H)

$^1$H-NMR measurement of the obtained compound (3F) (In Formula (3F), mf and nf indicating the average degree of polymerization was 4.5) was carried out, and the structure was identified from the following results.

Compound (3F); $^1$H-NMR ($CD_3COCD_3$);

δ [ppm] 1.3-1.7 (8H), 3.4-4.2 (24H)

$^1$H-NMR measurement of the obtained compound (3G) (In Formula (3G), mg and ng indicating the average degree of polymerization was 4.5) was carried out, and the structure was identified from the following results.

Compound (3G); $^1$H-NMR ($CD_3COCD_3$);

δ [ppm] 1.3-1.7 (10H), 3.4-4.2 (24H)

$^1$H-NMR measurement of the obtained compound (3H) (In Formula (3H), mh and nh indicating the average degree of polymerization was 4.5) was carried out, and the structure was identified from the following results.

Compound (3H); $^1$H-NMR ($CD_3COCD_3$);

δ [ppm] 1.3-1.7 (14H), 3.4-4.2 (24H)

$^1$H-NMR measurement of the obtained compound (3I) (In Formula (3I), mi and ni indicating the average degree of polymerization was 4.5) was carried out, and the structure was identified from the following results.

Compound (3I); $^1$H-NMR ($CD_3COCD_3$);

δ [ppm] 1.3-1.7 (4H), 3.4-4.2 (30H)

$^1$H-NMR measurement of the obtained compound (3J) (In Formula (3J), mj and nj indicating the average degree of polymerization was 4.5) was carried out, and the structure was identified from the following results.

Compound (3J); $^1$H-NMR ($CD_3COCD_3$);

δ [ppm] 1.5-1.8 (8H), 3.4-4.2 (22H)

$^1$H-NMR measurement of the obtained compound (3K) (In Formula (3K), mk and nk indicating the average degree of polymerization was 4.5) was carried out, and the structure was identified from the following results.

Compound (3K); $^1$H-NMR ($CD_3COCD_3$);

δ [ppm] 1.5-1.8 (411), 3.4-4.2 (28H)

$^1$H-NMR measurement of the obtained compound (3L) (In Formula (3L), ml and nl indicating the average degree of polymerization was 4.5) was carried out, and the structure was identified from the following results.

Compound (3L); $^1$H-NMR ($CD_3COCD_3$);

δ [ppm] 1.3-1.7 (8H), 3.4-4.2 (26H)

$^1$H-NMR measurement of the obtained compound (3M) (In Formula (3M), mm and nm indicating the average degree of polymerization was 4.5) was carried out, and the structure was identified from the following results.

Compound (3M); $^1$H-NMR ($CD_3COCD_3$);

δ [ppm] 1.5-1.8 (6H), 3.4-4.2 (28H)

$^1$H-NMR measurement of the obtained compound (3N) (In Formula (3N), mn and nn indicating the average degree of polymerization were 4.5) was carried out, and the structure was identified from the following results.

Compound (3N); $^1$H-NMR ($CD_3COCD_3$);

δ [ppm] 1.5-1.8 (8H), 3.4-4.2 (28H)

$^1$H-NMR measurement of the obtained compound (3P) (In Formula (3P), mp and np indicating the average degree of polymerization was 4.5) was carried out, and the structure was identified from the following results.

Compound (3P); $^1$H-NMR ($CD_3COCD_3$);

δ [ppm] 1.5-1.8 (12H), 3.4-4.2 (28H)

Comparative Example 1

A compound represented by Formula (S) below was synthesized by the method described in Patent Document 1.

$$HO—CH_2CH(OH)CH_2O—CH_2—CF_2CF_2O(C_3F_6O)_{zs}CF_2CF_2—CH_2—OCH_2CH(OH)CH_2—OH \quad (S)$$

(In Formula (S), zs indicating the average degree of polymerization was 4.5.)

Comparative Example 2

A compound represented by Formula (T) below was synthesized by the method described in Patent Document 2.

$$HOCH_2CH_2O—CH_2CH(OH)CH_2O—CH_2—CF_2O(CF_2CF_2O)_{mt}(CF_2O)_{nt}CF_2—CH_2—OCH_2CH(OH)CH_2—OCH_2CH_2OH \quad (T)$$

(In Formula (T), mt indicating the average degree of polymerization is 4.5, and nt indicating the average degree of polymerization is 4.5.)

Comparative Example 3

A compound represented by Formula (U) below was synthesized by the method described in Patent Document 3.

(U)

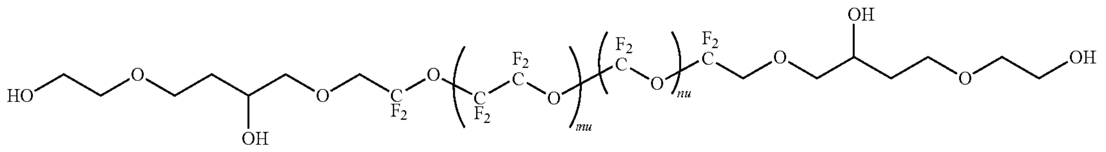

(In Formula (U), mu indicating the average degree of polymerization is 4.5, and nu indicating the average degree of polymerization is 4.5.)

Comparative Example 4

A compound represented by Formula (V) below was synthesized by the method described in Patent Document 3.

(V)

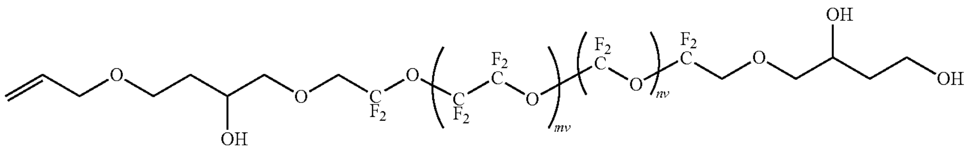

(In Formula (V), mv indicating the average degree of polymerization is 4.5, and nv indicating the average degree of polymerization is 4.5.)

Comparative Example 5

A compound represented by Formula (W) below was synthesized by the method described in Patent Document 4.

(W)

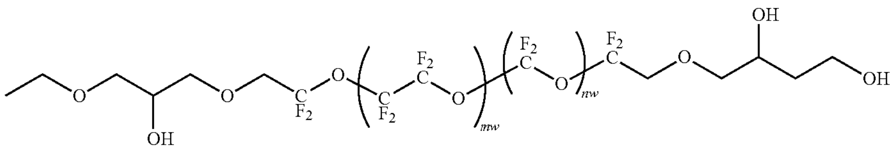

(In Formula (W), mw indicating the average degree of polymerization is 4.5, and nw indicating the average degree of polymerization is 4.5.)

Comparative Example 6

A compound represented by Formula (X) below was synthesized by the method described in Patent Document 4.

(X)

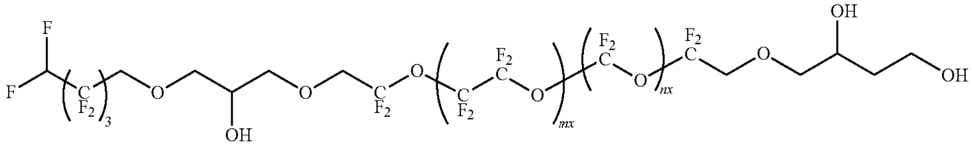

(In Formula (X), mx indicating the average degree of polymerization is 4.5, and nx indicating the average degree of polymerization is 4.5.)

The structures of $R^1$ and $R^5$, the structure of $R^2$ (a, b, and c in Formula (2)), the structure of $R^3$, and the structure of $R^4$ (d, e, and f in Formula (3)) when the compounds of Examples 1 to 45 and Comparative Examples 1 to 6 thus obtained are adapted to Formula (1) are shown in Tables 1 to 4.

TABLE 1

| | | | $R^2$ Formula (2) | | | | $R^4$ Formula (3) | | | | Number average molecular weight |
|---|---|---|---|---|---|---|---|---|---|---|---|
| | Compound | $R^1$ | c | b | a | $R^3$ | d | e | f | $R^5$ | (Mn) |
| Example 1 | 1A | H | 2 | 1 | 0 | Formula (7) z = 4.5 | 0 | 1 | 2 | H | 1201 |
| Example 2 | 1B | H | 3 | 1 | 0 | Formula (7) z = 4.5 | 0 | 1 | 3 | H | 1229 |
| Example 3 | 1C | H | 4 | 1 | 0 | Formula (7) z = 4.5 | 0 | 1 | 4 | H | 1257 |

TABLE 1-continued

| | Compound | $R^1$ | $R^2$ Formula (2) c | b | a | $R^3$ | $R^4$ Formula (3) d | e | f | $R^5$ | Number average molecular weight (Mn) |
|---|---|---|---|---|---|---|---|---|---|---|---|
| Example 4 | 1D | H | 5 | 1 | 0 | Formula (7) z = 4.5 | 0 | 1 | 5 | H | 1285 |
| Example 5 | 1E | H | 2 | 1 | 0 | Formula (7) z = 4.5 | 1 | 1 | 2 | H | 1275 |
| Example 6 | 1F | H | 4 | 1 | 0 | Formula (7) z = 4.5 | 1 | 1 | 2 | H | 1303 |
| Example 7 | 1G | H | 5 | 1 | 0 | Formula (7) z = 4.5 | 1 | 1 | 2 | H | 1317 |
| Example 8 | 1H | H | 4 | 1 | 0 | Formula (7) z = 4.5 | 1 | 1 | 4 | H | 1331 |
| Example 9 | 1I | H | 2 | 1 | 1 | Formula (7) z = 4.5 | 1 | 1 | 2 | H | 1349 |
| Example 10 | 1J | Formula (4) k = 3 | — | 0 | 1 | Formula (7) z = 4.5 | 0 | 1 | 4 | H | 1273 |
| Example 11 | 1K | Formula (4) k = 3 | — | 0 | 1 | Formula (7) z = 4.5 | 1 | 1 | 2 | H | 1319 |
| Example 12 | 1L | Formula (4) k = 3 | 2 | 1 | 0 | Formula (7) z = 4.5 | 0 | 1 | 2 | Formula (4) k = 3 | 1317 |
| Example 13 | 1M | Formula (4) k = 3 | 2 | 1 | 0 | Formula (7) z = 4.5 | 1 | 1 | 2 | H | 1333 |
| Example 14 | 1N | Formula (4) k = 3 | 3 | 1 | 0 | Formula (7) z = 4.5 | 1 | 1 | 2 | H | 1347 |
| Example 15 | 1P | Formula (4) k = 6 | 2 | 1 | 0 | Formula (7) z = 4.5 | 1 | 1 | 2 | H | 1376 |

TABLE 2

| | Compound | $R^1$ | $R^2$ Formula (2) c | b | a | $R^3$ | $R^4$ Formula (3) d | e | f | $R^5$ | Number average molecular weight (Mn) |
|---|---|---|---|---|---|---|---|---|---|---|---|
| Example 16 | 2A | H | 2 | 1 | 0 | Formula (5) m = 7.0, n = 0 | 0 | 1 | 2 | H | 1166 |
| Example 17 | 2B | H | 3 | 1 | 0 | Formula (5) m = 7.0, n = 0 | 0 | 1 | 3 | H | 1194 |
| Example 18 | 2C | H | 4 | 1 | 0 | Formula (5) m = 7.0, n = 0 | 0 | 1 | 4 | H | 1222 |
| Example 19 | 2D | H | 5 | 1 | 0 | Formula (5) m = 7.0, n = 0 | 0 | 1 | 5 | H | 1250 |
| Example 20 | 2E | H | 2 | 1 | 0 | Formula (5) m = 7.0, n = 0 | 1 | 1 | 2 | H | 1240 |
| Example 21 | 2F | H | 4 | 1 | 0 | Formula (5) m = 7.0, n = 0 | 1 | 1 | 2 | H | 1268 |
| Example 22 | 2G | H | 5 | 1 | 0 | Formula (5) m = 7.0, n = 0 | 1 | 1 | 2 | H | 1282 |
| Example 23 | 2H | H | 4 | 1 | 0 | Formula (5) m = 7.0, n = 0 | 1 | 1 | 4 | H | 1296 |
| Example 24 | 2I | H | 2 | 1 | 1 | Formula (5) m = 7.0, n = 0 | 1 | 1 | 2 | H | 1314 |
| Example 25 | 2J | Formula (4) k = 3 | — | 0 | 1 | Formula (5) m = 7.0, n = 0 | 0 | 1 | 4 | H | 1238 |
| Example 26 | 2K | Formula (4) k = 3 | — | 0 | 1 | Formula (5) m = 7.0, n = 0 | 1 | 1 | 2 | H | 1284 |
| Example 27 | 2L | Formula (4) k = 3 | 2 | 1 | 0 | Formula (5) m = 7.0, n = 0 | 0 | 1 | 2 | Formula (4) k = 3 | 1282 |
| Example 28 | 2M | Formula (4) k = 3 | 2 | 1 | 0 | Formula (5) m = 7.0, n = 0 | 1 | 1 | 2 | H | 1298 |
| Example 29 | 2N | Formula (4) k = 3 | 3 | 1 | 0 | Formula (5) m = 7.0, n = 0 | 1 | 1 | 2 | H | 1312 |
| Example 30 | 2P | Formula (4) k = 6 | 2 | 1 | 0 | Formula (5) m = 7.0, n = 0 | 1 | 1 | 2 | H | 1341 |

TABLE 3

| | | | R² Formula (2) | | | | R⁴ Formula (3) | | | | Number average molecular weight |
|---|---|---|---|---|---|---|---|---|---|---|---|
| | Compound | $R^1$ | c | b | a | $R^3$ | d | e | f | $R^5$ | (Mn) |
| Example 31 | 3A | H | 2 | 1 | 0 | Formula (5) m = 4.5, n = 4.5 | 0 | 1 | 2 | H | 1173 |
| Example 32 | 3B | H | 3 | 1 | 0 | Formula (5) m = 4.5, n = 4.5 | 0 | 1 | 3 | H | 1201 |
| Example 33 | 3C | H | 4 | 1 | 0 | Formula (5) m = 4.5, n = 4.5 | 0 | 1 | 4 | H | 1229 |
| Example 34 | 3D | H | 5 | 1 | 0 | Formula (5) m = 4.5, n = 4.5 | 0 | 1 | 5 | H | 1257 |
| Example 35 | 3E | H | 2 | 1 | 0 | Formula (5) m = 4.5, n = 4.5 | 1 | 1 | 2 | H | 1247 |
| Example 36 | 3F | H | 4 | 1 | 0 | Formula (5) m = 4.5, n = 4.5 | 1 | 1 | 2 | H | 1275 |
| Example 37 | 3G | H | 5 | 1 | 0 | Formula (5) m = 4.5, n = 4.5 | 1 | 1 | 2 | H | 1289 |
| Example 38 | 3H | H | 4 | 1 | 0 | Formula (5) m = 4.5, n = 4.5 | 1 | 1 | 4 | H | 1303 |
| Example 39 | 3I | H | 2 | 1 | 1 | Formula (5) m = 4.5, n = 4.5 | 1 | 1 | 2 | H | 1321 |
| Example 40 | 3J | Formula (4) k = 3 | — | 0 | 1 | Formula (5) m = 4.5, n = 4.5 | 0 | 1 | 4 | H | 1245 |
| Example 41 | 3K | Formula (4) k = 3 | — | 0 | 1 | Formula (5) m = 4.5, n = 4.5 | 1 | 1 | 2 | H | 1291 |
| Example 42 | 3L | Formula (4) k = 3 | 2 | 1 | 0 | Formula (5) m = 4.5, n = 4.5 | 0 | 1 | 2 | Formula (4) k = 3 | 1289 |
| Example 43 | 3M | Formula (4) k = 3 | 2 | 1 | 0 | Formula (5) m = 4.5, n = 4.5 | 1 | 1 | 2 | H | 1305 |
| Example 44 | 3N | Formula (4) k = 3 | 3 | 1 | 0 | Formula (5) m = 4.5, n = 4.5 | 1 | 1 | 2 | H | 1319 |
| Example 45 | 3P | Formula (4) k = 6 | 2 | 1 | 0 | Formula (5) m = 4.5, n = 4.5 | 1 | 1 | 2 | H | 1348 |

TABLE 4

| | | | R² Formula (2) | | | | R⁴ Formula (3) | | | | Number average molecular weight |
|---|---|---|---|---|---|---|---|---|---|---|---|
| | Compound | $R^1$ | c | b | a | $R^3$ | d | e | f | $R^5$ | (Mn) |
| Comparative Example 1 | S | H | — | 0 | 1 | Formula (7) z = 4.5 | 1 | 0 | — | H | 1172 |
| Comparative Example 2 | T | Formula (4) k = 2 | — | 0 | 1 | Formula (5) m = 4.5, n = 4.5 | 1 | 0 | — | Formula (4) k = 2 | 1233 |
| Comparative Example 3 | U | Formula (4) k = 2 | 2 | 1 | 0 | Formula (5) m = 4.5, n = 4.5 | 0 | 1 | 2 | Formula (4) k = 2 | 1261 |
| Comparative Example 4 | V | Allyl group | 2 | 1 | 0 | Formula (5) m = 4.5, n = 4.5 | 0 | 1 | 2 | H | 1213 |
| Comparative Example 5 | W | Ethyl group | — | 0 | 1 | Formula (5) m = 4.5, n = 4.5 | 0 | 1 | 2 | H | 1187 |
| Comparative Example 6 | X | 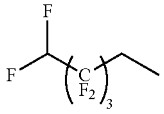 | — | 0 | 1 | Formula (5) m = 4.5, n = 4.5 | 0 | 1 | 2 | H | 1369 |

In addition, the number average molecular weights (Mn) of the compounds of Examples 1 to 45 and Comparative Examples 1 to 6 were obtained by the $^1$H-NMR and $^{19}$F-NMR measurement. The results are shown in Tables 1 to 4. It is inferred that, in the values of the average molecular weight of the synthesized compounds, variations of approximately 1 to 5 may exist depending on, for example, the molecular weight distributions of the fluoropolyether used as a raw material of the compounds and differences in the operation at the time of synthesizing the compounds.

Next, solutions for forming a lubricating layer were prepared using the compounds obtained in Examples 1 to 45 and Comparative Examples 1 to 6 by a method shown below. Moreover, lubricating layers of magnetic recording media were formed using the obtained solutions for forming a lubricating layer by a method shown below, and magnetic recording media of Examples 1 to 45 and Comparative Examples 1 to 6 were obtained.

"Solutions for Forming Lubricating Layer"

The compounds obtained in Examples 1 to 45 and Comparative Examples 1 to 6 were each dissolved in VERTREL (registered trademark) XF (trade name, manufactured by Dupont-Mitsui Fluorochemicals Co., Ltd.), which is a fluorine-based solvent, diluted with VERTREL such that these have a film thickness of about 9 Å when applied onto protective layers, and used as solutions for forming a lubricating layer.

"Magnetic Recording Media"

Magnetic recording media each having an adhesive layer, a soft magnetic layer, a first underlayer, a second underlayer, a magnetic layer, and a protective layer sequentially provided on a substrate having a diameter of 65 mm were prepared. As the protective layer, a carbon layer with a thickness of 2.7 nm was used.

The solutions for forming a lubricating layer of Examples 1 to 45 and Comparative Examples 1 to 6 were each applied onto the protective layers of the magnetic recording media, in which the individual layers up to the protective layer had been formed, by the dipping method. The dipping method was carried out under conditions of an immersion speed of 10 mm/sec, an immersion time of 30 seconds and a lifting speed of 1.2 mm/sec.

Thereafter, a burnishing step was performed in which burnishing tape holding abrasive grains having a grain size #6000 was scanned on the surface of each of the magnetic recording media on which the lubricating layer was formed.

The magnetic recording media after the burnishing step were placed in a thermostatic chamber at 120° C. to perform a heat treatment for 10 minutes.

Magnetic recording media (which were burnished) of Examples 1 to 45 and Comparative Examples 1 to 6 were obtained through the above-described steps.

In addition, magnetic recording media (which were unburnished) of Examples 1 to 45 and Comparative Examples 1 to 6 were obtained in the same manner as the burnished magnetic recording media except that a burnishing step was not performed.

(Film Thickness Measurement)

The film thicknesses of the lubricating layers in the magnetic recording media (which were unburnished) of Examples 1 to 45 and Comparative Examples 1 to 6 thus obtained were measured using FT-IR (trade name: Nicolet iS50, manufactured by Thermo Fisher Scientific Inc.). The results are shown in Tables 5 to 8.

TABLE 5

| | Film thickness (Å) | Unburnished | Burnished |
|---|---|---|---|
| Example 1 | 9.0 | A | A |
| Example 2 | 9.0 | A | A |
| Example 3 | 9.1 | A | A |
| Example 4 | 9.1 | A | A |
| Example 5 | 9.0 | A | B |
| Example 6 | 9.0 | A | A |
| Example 7 | 8.9 | A | A |
| Example 8 | 9.0 | A | A |
| Example 9 | 9.0 | B | B |
| Example 10 | 9.1 | A | A |
| Example 11 | 9.0 | A | B |
| Example 12 | 9.0 | A | B |
| Example 13 | 8.9 | A | B |
| Example 14 | 8.9 | A | B |
| Example 15 | 9.1 | A | A |

TABLE 6

| | Film thickness (Å) | Unburnished | Burnished |
|---|---|---|---|
| Example 16 | 9.0 | A | B |
| Example 17 | 9.0 | A | A |
| Example 18 | 8.9 | A | A |
| Example 19 | 9.1 | A | A |

TABLE 6-continued

| | Film thickness (Å) | Unburnished | Burnished |
|---|---|---|---|
| Example 20 | 9.1 | A | B |
| Example 21 | 9.1 | A | A |
| Example 22 | 9.1 | A | A |
| Example 23 | 9.1 | A | A |
| Example 24 | 8.9 | B | B |
| Example 25 | 9.0 | A | B |
| Example 26 | 8.9 | A | B |
| Example 27 | 9.0 | A | B |
| Example 28 | 8.9 | A | B |
| Example 29 | 9.1 | A | B |
| Example 30 | 9.1 | A | B |

TABLE 7

| | Film thickness (Å) | Unburnished | Burnished |
|---|---|---|---|
| Example 31 | 9.1 | A | B |
| Example 32 | 8.9 | A | A |
| Example 33 | 9.0 | A | A |
| Example 34 | 9.0 | A | A |
| Example 35 | 9.0 | A | B |
| Example 36 | 9.0 | A | A |
| Example 37 | 9.0 | A | A |
| Example 38 | 9.0 | A | A |
| Example 39 | 9.1 | B | B |
| Example 40 | 8.9 | A | B |
| Example 41 | 9.0 | A | B |
| Example 42 | 9.1 | A | B |
| Example 43 | 9.0 | A | B |
| Example 44 | 8.9 | B | B |
| Example 45 | 9.0 | A | B |

TABLE 8

| | Film thickness (Å) | Unburnished | Burnished |
|---|---|---|---|
| Comparative Example 1 | 9.0 | C | E |
| Comparative Example 2 | 8.9 | C | E |
| Comparative Example 3 | 9.1 | C | D |
| Comparative Example 4 | 9.0 | C | D |
| Comparative Example 5 | 9.0 | C | D |
| Comparative Example 6 | 9.1 | C | D |

Next, corrosion resistance tests shown below were performed on the burnished and unburnished magnetic recording media of Examples 1 to 45 and Comparative Examples 1 to 6.

(Corrosion Resistance Tests)

The magnetic recording media were exposed to conditions of 85° C. and a relative humidity of 90% for 48 hours. Thereafter, number of corroded spots of the magnetic recording media was counted using an optical surface analyzer and evaluated based on the following evaluation criteria. The results are shown in Tables 5 to 8.

"Evaluation Criteria"

A: 500 or less

B: 501 to 1,000

C: 1,001 to 1,500

D: 1501 to 2,000

E: Greater than or equal to 2001

As shown in Tables 5 to 7, in both cases of the burnished and unburnished magnetic recording media of Examples 1 to 45 having a lubricating layer containing the compound represented by Formula (1), the results of the corrosion resistance tests were A or B, which showed favorable corrosion resistance. It is inferred that this could be achieved because the compound represented by Formula (1) contained in the lubricating layers of the magnetic recording media of Examples 1 to 45 has both hydrophilic parts (four to six hydroxyl groups) and hydrophobic parts (a PFPE chain and two or more linearly bound methylene groups) in the molecule.

In particular, in cases where $R^3$ in Formula (1) is Formula (7) having a repeating unit containing three linearly bound $—CF_2—$ (for example, Examples 1, 10, and 15), the results of the corrosion resistance tests in the burnished case were favorable compared to cases where $R^3$ is Formula (5) having a repeating unit containing two linearly bound $—CF_2—$ (for example, Examples 16, 25, 30, 31, 40, and 45).

In addition, in cases where c in Formula (2) is 4 (for example, Examples 6, 21, and 36), the results of the corrosion resistance tests in the burnished case were favorable compared to cases where c in Formula (2) is 2 (for example, Examples 5, 20, and 35). In addition, in a case where f in Formula (3) is 4 (for example, Example 10), the results of the corrosion resistance tests in the burnished case were favorable compared to a case where f in Formula (2) is 2 (for example, Example 11).

In addition, in cases where a and b in Formula (2) are respectively 0 and 1 and d and e in Formula (3) are respectively 0 and 1 (for example, Examples 1, 16, and 31), the results of the corrosion resistance tests in the burnished and/or unburnished cases were favorable compared to cases where a and b in Formula (2) are 1 and d and e in Formula (3) are 1 (for example, Examples 9, 24, and 39).

In addition, in a case where $R^1$ in Formula (1) is Formula (4) where k is 6 (for example, Example 15), the results of the corrosion resistance tests in the burnished case were favorable compared to a case where $R^1$ in Formula (1) is a hydrogen atom (for example, Example 5).

On the other hand, in the magnetic recording media of Comparative Example 1 in which both b in Formula (2) and e in Formula (3) are 0, Comparative Example 2 in which both b in Formula (2) and e in Formula (3) are 0 and $R^1$ and $R^5$ in Formula (1) are Formula (4) where k is 2, Comparative Example 3 in which $R^1$ and $R^5$ in Formula (1) are Formula (4) where k is 2, and Comparative Examples 4 to 6 in which $R^1$ in Formula (1) is not a hydrogen atom or Formula (4), the results of the corrosion resistance tests were C in the unburnished case and D or E in the burnished case as shown in Table 8, which was inferior corrosion resistance compared to the magnetic recording media of Examples 1 to 45.

INDUSTRIAL APPLICABILITY

By using the lubricant for a magnetic recording medium containing the fluorine-containing ether compound of the present invention, a lubricating layer capable of realizing excellent corrosion resistance even if the lubricating layer has a thin thickness can be formed.

REFERENCE SIGNS LIST

10 Magnetic recording medium
11 Substrate
12 Adhesive layer
13 Soft magnetic layer
14 First underlayer
15 Second underlayer
16 Magnetic layer
17 Protective layer
18 Lubricating layer

The invention claimed is:

1. A fluorine-containing ether compound represented by any of Formulae (1E) to (1I), (1K), (1M), (1N), (1P), (2E) to (2I), (2K), (2M), (2N), (2P), (3E) to (3I), (3K), (3M), (3N), and (3P)

(1E)

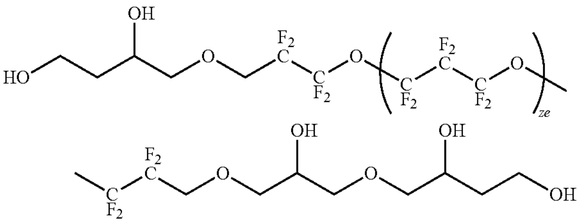

(1F)

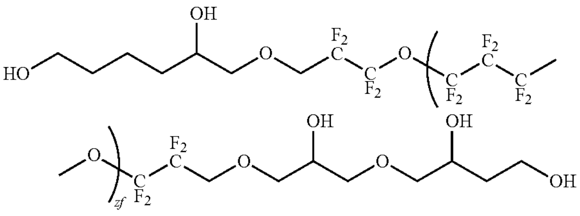

(1G)

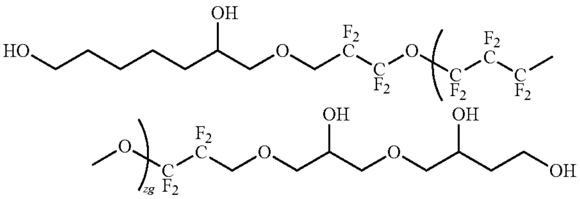

(ze in Formula (1E) indicates an average degree of polymerization and represents 0.1 to 30), (zf in Formula (1F) indicates an average degree of polymerization and represents 0.1 to 30), (zg in Formula (1G) indicates an average degree of polymerization and represents 0.1 to 30),

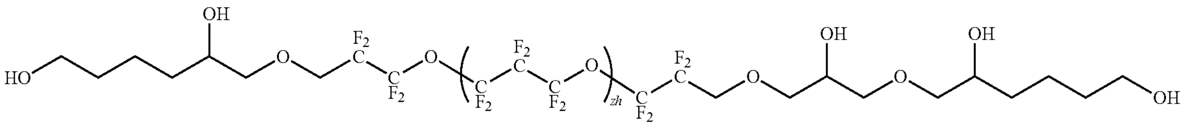

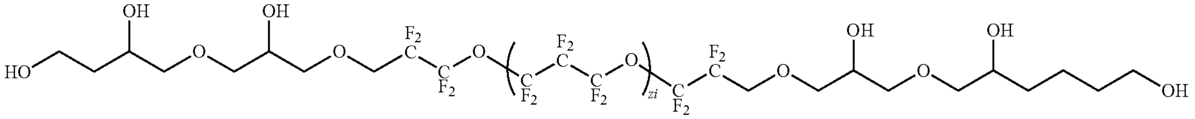

-continued

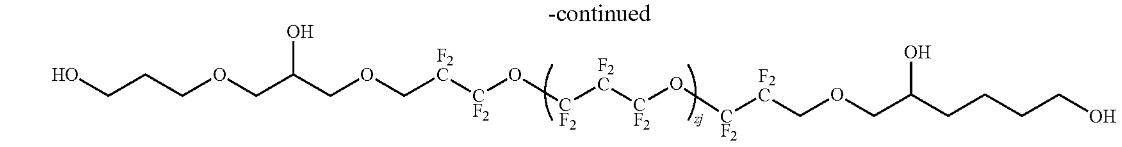

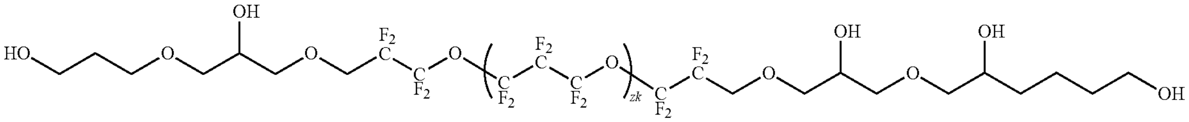

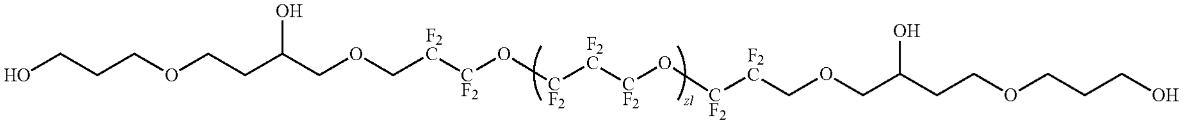

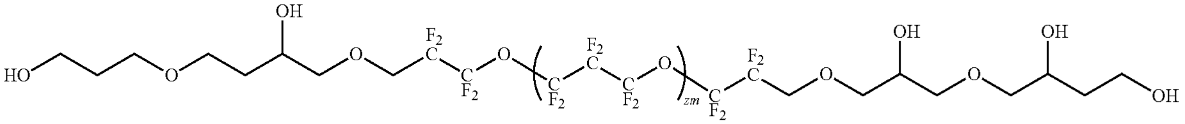

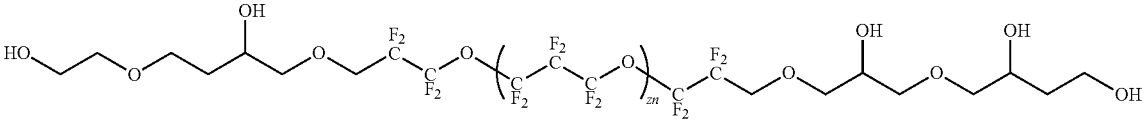

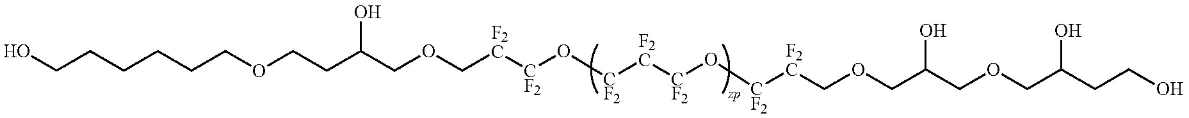

(zh in Formula (1H) indicates an average degree of polymerization and represents 0.1 to 30), (zi in Formula (1I) indicates an average degree of polymerization and represents 0.1 to 30), (zk in Formula (1K) indicates an average degree of polymerization and represents 0.1 to 30), (zm in Formula (1M) indicates an average degree of polymerization and represents 0.1 to 30), (zn in Formula (1N) indicates an average degree of polymerization and represents 0.1 to 30), (zp in Formula (1P) indicates an average degree of polymerization and represents 0.1 to 30), (2E)

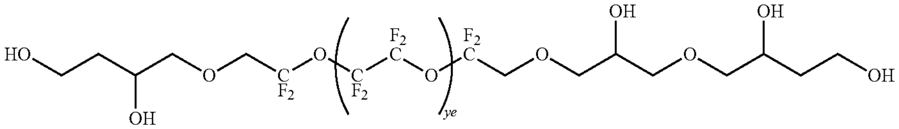

(2F)

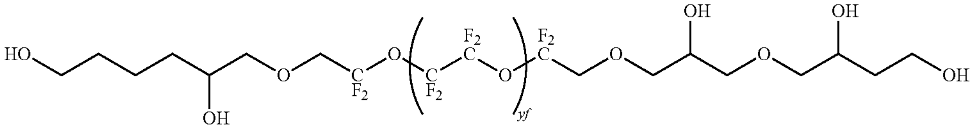

(2G)

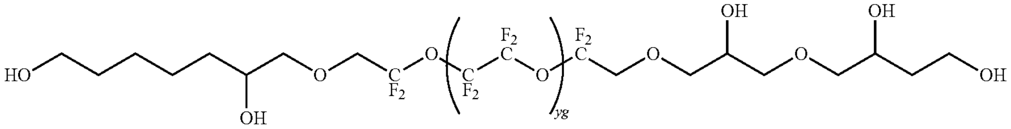

(ye in Formula (2E) indicates an average degree of polymerization and represents 0.1 to 30), (yf in Formula (2F) indicates an average degree of polymerization and represents 0.1 to 30), (yg in Formula (2G) indicates an average degree of polymerization and represents 0.1 to 30),

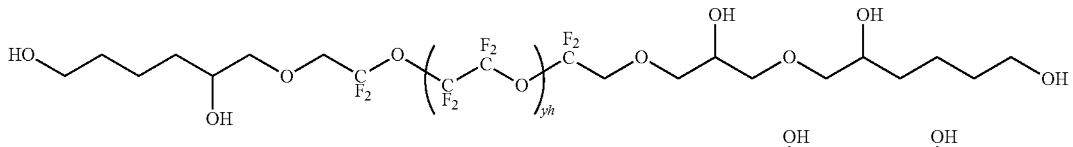

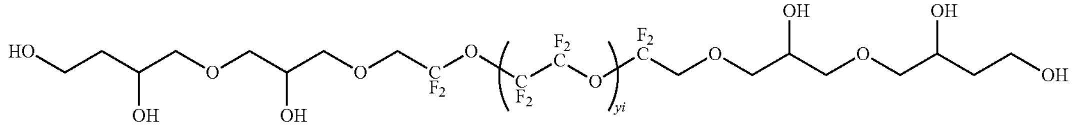

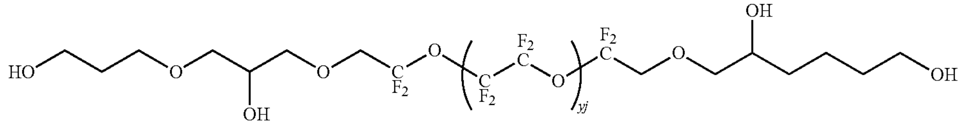

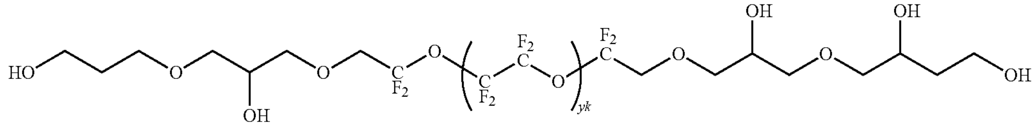

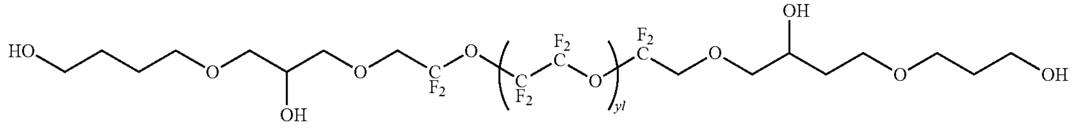

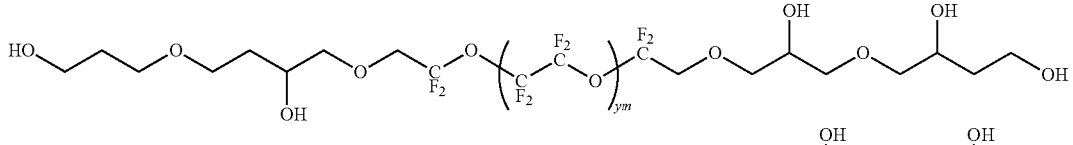

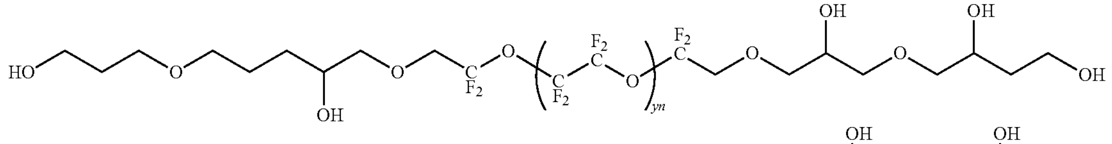

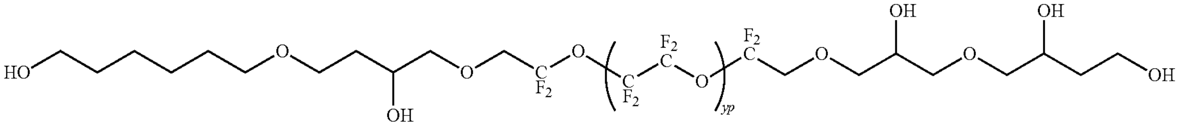

(yh in Formula (2H) indicates an average degree of polymerization and represents 0.1 to 30), (yi in Formula (2I) indicates an average degree of polymerization and represents 0.1 to 30), (yk in Formula (2K) indicates an average degree of polymerization and represents 0.1 to 30), (ym in Formula (2M) indicates an average degree of polymerization and represents 0.1 to 30), (yn in Formula (2N) indicates an average degree of polymerization and represents 0.1 to 30), (yp in Formula (2P) indicates an average degree of polymerization and represents 0.1 to 30), (3E)

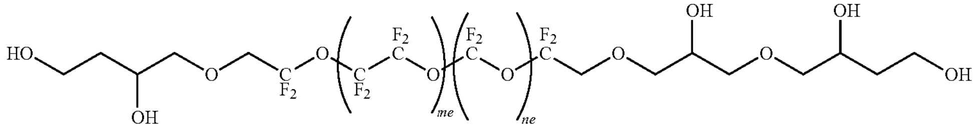

(3F)

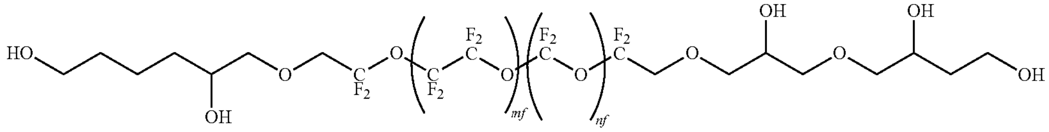

-continued (3G)

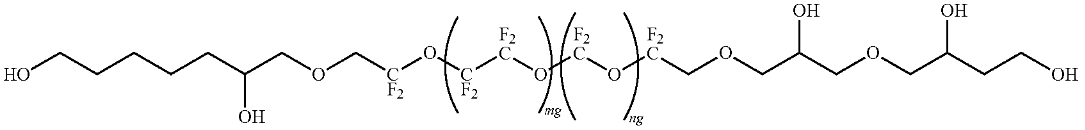

(me and ne in Formula (3E) indicate an average degree of polymerization and represent 0.1 to 30), (mf and nf in Formula (3F) indicate an average degree of polymerization and represent 0.1 to 30), (mg and ng in Formula (3G) indicate an average degree of polymerization and represent 0.1 to 30),

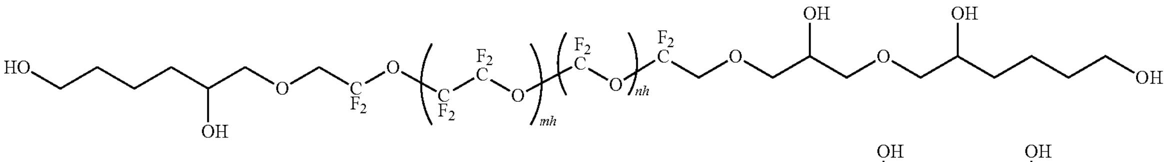

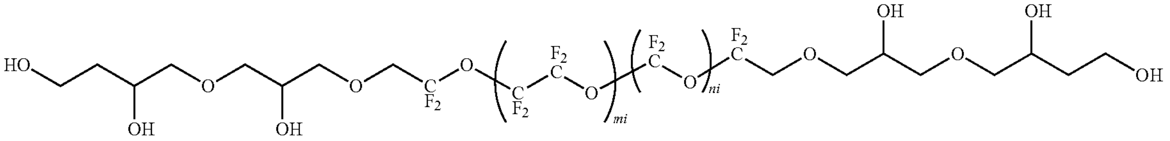

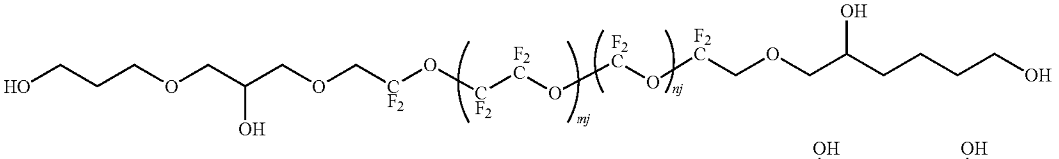

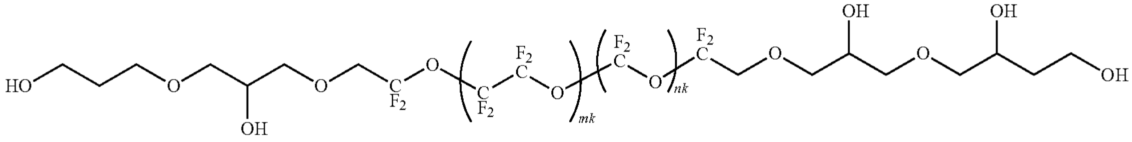

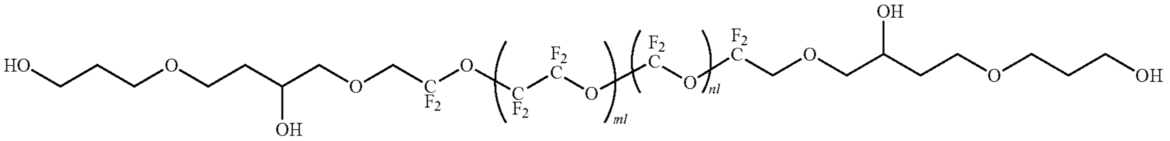

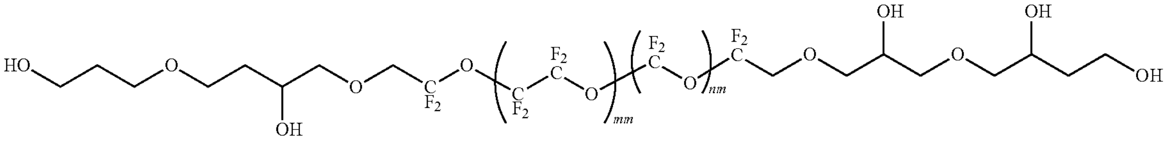

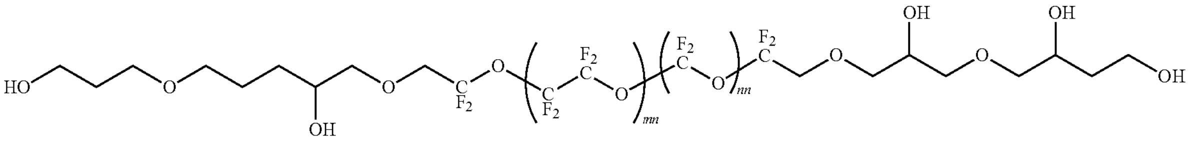

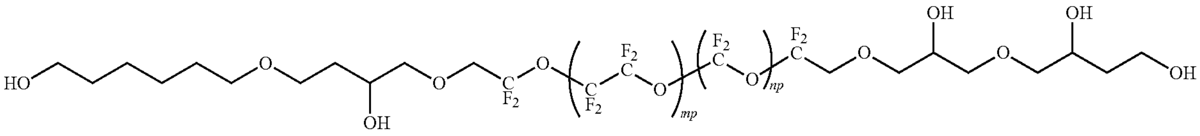

(mh and nh in Formula (3H) indicate an average degree of polymerization and represent 0.1 to 30), (mi and ni in Formula (3I) indicate an average degree of polymerization and represent 0.1 to 30), (mk and nk in Formula (3K) indicate an average degree of polymerization and represent 0.1 to 30), (mm and nm in Formula (3M) indicate an average degree of polymerization and represent 0.1 to 30), (mn and nn in Formula (3N) indicate an average degree of polymerization and represent 0.1 to 30), (mp and np in Formula (3P) indicate an average degree of polymerization and represent 0.1 to 30).

2. The fluorine-containing ether compound according to claim 1, wherein a number average molecular weight thereof is within a range of 500 to 10,000.

3. A lubricant for a magnetic recording medium comprising:

the fluorine-containing ether compound according to claim 1.

4. A magnetic recording medium, wherein at least a magnetic layer, a protective layer, and a lubricating layer are sequentially provided on a substrate, and wherein the lubricating layer contains the fluorine-containing ether compound according to claim 1.

5. The magnetic recording medium according to claim 4, wherein an average film thickness of the lubricating layer is 0.5 nm to 2.0 nm.

* * * * *